(12) United States Patent
Toyoshima et al.

(10) Patent No.: US 8,236,758 B2
(45) Date of Patent: Aug. 7, 2012

(54) METHOD OF TREATMENT OF DIABESTES OR REDUCTION IN PANCREATIC BETA-CELLS

(75) Inventors: Hideo Toyoshima, Tokyo (JP); Tomotaka Yokoo, Tsukuba (JP); Nobuhiro Yamada, Tokyo (JP)

(73) Assignee: Saitama Medical University, Saitama (JP)

( * ) Notice: Subject to any disclaimer, the term of this patent is extended or adjusted under 35 U.S.C. 154(b) by 0 days.

(21) Appl. No.: 12/669,324

(22) PCT Filed: Jul. 20, 2007

(86) PCT No.: PCT/JP2007/064537
§ 371 (c)(1),
(2), (4) Date: Jan. 15, 2010

(87) PCT Pub. No.: WO2009/013794
PCT Pub. Date: Jan. 29, 2009

(65) Prior Publication Data
US 2010/0168026 A1 Jul. 1, 2010

(51) Int. Cl.
*A61K 38/00* (2006.01)
(52) U.S. Cl. ....... 514/6.9; 514/21.2; 514/21.4; 530/300; 530/350
(58) Field of Classification Search .................. None
See application file for complete search history.

(56) References Cited

OTHER PUBLICATIONS

Wells, 1990, Biochemistry 29:8509-8517.*
Bowie et al., 1990, Science 247: 1306-1310.*
Mickle et al., Med. Clin. North Am., vol. 84(3), p. 597-607, 2000.*
Verploegen et al., FEBS Letters 405, 237-240, 1997.*
Yokoo, Tomotaka et al., "Research on development of novel remedy in type II diabetes," Choju Kagaku Sogo Kenkyu Suishin Jigyo Kenkyu Hokokushu, Heisei 17 Nendo (2006 Nen) pp. 361-364, refer to pp. 363-364 "(3) Seika".
Toyoshima, Hideo et al., "Identification and analysis of a novel alimentrary-specific secretory protein gene CF266," Folia Endocrinologica Japonica, Apr. 20, 2007, vol. 83, No. 1, p. 103, refer to summary described in lowest part of left column.
Toyoshima et al., "Functional analysis of CF266, a novel alimentary-specific secretory protein having insulin secretion-stimulating function," The Journal of the Japan Diabetic Society, Apr. 25, 2007, vol. 50 (Supplement 1), p. S284, refer to the summary described in the lowest part of the left column.
Strausberg, R.L. et al, "Generation and initial analysis of more than 15,000 full-length human and mouse cDNA sequences," Proc. Natl. Acad. USA, 2002, vol. 99, No. 26, pp. 16899-16903.
Extended European Search Report mailed Jul. 12, 2010 in European Patent Application No. 07791094.1.
Database Geneseq [Online] Mar. 11, 2004, "Human secreted/transmembrane protein PRO994." XP002588764 retrieved from EBI accession No. GSP:ADH20997 Database accession No. ADH20997.
Database Geneseq [Online] Oct. 21, 2004, "Human NF-kappaB pathway-associated gene SeqID507." XP002588769 retrieved from EBI accession No. GSN:ADR14506 Database accession No. ADR14506.
Database UniProt [Online] May 24, 2005, "RecName: Full=Transmembrane 4 L6 family member 20;" XP002588765 retrieved from EBI accession No. UNIPROT:Q53R12 Database accession No. Q53R12.
Database UniProt [Online] Jun. 1, 2001, "RecName: Full=Transmembrane 4 L6 family member 20;" XP002588776 retrieved from EBI accession No. UNIPROT:Q9CQY8 Database accession No. Q9CQY8.
Database Geneseq [Online] May 3, 2007, "Human de-differentiated cell marker gene SEQ ID No:347." XP002588766 retrieved from EBI accession No. GSN:AFH54246 Database accession No. AFH54246.
Database Geneseq [Online] May 19, 2005, "Human colorectal cancer assoicated gene SEQ ID No:47." XP002588767 retrieved from EBI accession No. GSN:ADX44427 Database accession No. ADX44427.
Database Geneseq [Online] Oct. 21, 2004, "Human NF-kappaB pathway-associated protein SeqID508." XP002588768 retrieved from EBI accession No. GSP:ADR14507 Database accession No. ADR14507.

* cited by examiner

*Primary Examiner* — Gyan Chandra
(74) *Attorney, Agent, or Firm* — Dilworth & Barrese, LLP

(57) ABSTRACT

Disclosed are: an insulin secretion inducer; an insulin secretion-inducing composition; a process for the production of the composition; an accelerator for increasing the number of pancreatic β-cells; a composition for increasing the number of pancreatic β-cells; a process for the production of the composition; and a viral vector for gene therapy. The insulin secretion inducer or the accelerator for increasing the number of pancreatic β-cells comprises a polypeptide having an amino acid sequence encoded by DNA that is known to encode a membrane protein Tm4sf20 (transmembrane 4 L six family member 20) or the like or a fragment of the polypeptide as an active ingredient.

2 Claims, 6 Drawing Sheets

SEQUENCE LISTING

```
<160> NUMBER OF SEQ ID NOS: 12

<210> SEQ ID NO 1
<211> LENGTH: 1505
<212> TYPE: DNA
<213> ORGANISM: Mouse

<400> SEQUENCE: 1
gagccaccct gaggaggttt ctaactgaac caggaaaacc atgacgtgct gtgaagggtg      60
gacatcctgc aatggcttca gcctgctcat tctgatcctg ctaggagtgg ttatcaattg     120 tataccctg ggaatcagct tagtggaggc agactcgact tctcaaaacc ccatctcctg     180
ctatgagtgg tggtttccag gaattatagg agcaggtctg atggccatcc cagcaacaac     240
aatgtccttg gcagcaagaa aaagagcgtg ctgcaacaac aagactggga tgtttctttc     300
atcactcttc agtgtgatca cagttgttgg tgctgtgtat tgcatgttgg tatcactcca     360
ggctctcttg gaaggacctc taatttgtaa tactcaggcc aacagtactg tcacttgtga     420 atttcattg aaaaacttaa gtaaatttga tcctgaatcc ttcaatctgc tgtggttctt     480
caatggcact tgtgtttctc ctactgattt taaaaacccc accatcaata acatggtcag     540
taactggaaa atacccaact ccaactctga agaagacaga cacaggattt tccacttctc     600
agtatttatg agtctcctgc ttgttggaat cctggagctc ctgtttgggc tcagtcagat     660
actcattggt ttccttggct gtctgtgtgg cgtctctcag cgacggagtc aaattgtata     720
aagggcaata aactagaata tcagtacttt gaataatttg aaaattgcat ttaaaatata     780
tacttttgta agttcaataa tgaagcatct tctagaacac agagtcattt tagtgcaaac     840
agatgttttt agaatcatct ctgaagcaac tctcaaaaaa aaaattaacc tatcaagctg     900
ggcagggctg gtacaggcct tcgatcccag cactcaggag cagaggctgg aggattcaga     960
gtttgaggcc tgcctagttt acaaatgcca agacagccag gactatacag agaagctaaa    1020
gcagaggact ggcatgaact cgcactagcg cgtcctgtat gtgcagtgca cctccactcc    1080 gggggagaa gttaccagtg ggtgacacag gggagaagca taggaaagct tttaggtttc    1140 tttttccta tgtatgccaa aagaacaatt gtccacctca tcggttacag aagtatgtgt    1200
cttagtttta agaaatatat attatgtgtt ttgggaggaa gaccatgttt taaaaatact    1260
ttaccctcaa agccaaagtg atggaaaaat gctgtgttta actgacaggc acatggcaat    1320
tcatcatact ctattctttt atgtttgtat ctcttcatga tatctgctaa gactttgggg    1380
aaaaaaaatc agccttttag aagctggttt ttatgtatgc tgatctttaa aagataggta    1440
acaaaatgta tttattgtat taaaatgtta tgaaatagaa aaaactaaaa atctacaatt    1500
ttctg                                                                1505

<210> SEQ ID NO 2
<211> LENGTH: 1505
<212> TYPE: DNA
<213> ORGANISM: Mouse
<220> FEATURE:
<221> NAME/KEY: CDS
<222> LOCATION: (41)..(721)
<223> OTHER INFORMATION: coding sequence for insulin secretion inducer
```

```
<400> SEQUENCE: 2
gagccaccct gaggaggttt ctaactgaac caggaaaacc atg acg tgc tgt gaa        55
                                             Met Thr Cys Cys Glu
                                             1               5 ggg tgg aca tcc tgc aat ggc ttc agc ctc att ctg atc ctg cta           103
Gly Trp Thr Ser Cys Asn Gly Phe Ser Leu Ile Leu Ile Leu Leu
            10                  15                  20 gga gtg gtt atc aat tgt ata ccc ctg gga atc agc tta gtg gag gca      151
Gly Val Val Ile Asn Cys Ile Pro Leu Gly Ile Ser Leu Val Glu Ala
                25                  30                  35 gac tcg act tct caa aac ccc atc tcc tgc tat gag tgg tgg ttt cca      199
Asp Ser Thr Ser Gln Asn Pro Ile Ser Cys Tyr Glu Trp Trp Phe Pro
        40                  45                  50 gga att ata gga gca ggt ctg atg gcc atc cca gca aca aca atg tcc      247
Gly Ile Ile Gly Ala Gly Leu Met Ala Ile Pro Ala Thr Thr Met Ser
55                  60                  65 ttg gca gca aga aaa aga gcg tgc tgc aac aac aag act ggg atg ttt      295
Leu Ala Ala Arg Lys Arg Ala Cys Cys Asn Asn Lys Thr Gly Met Phe
70                  75                  80                  85 ctt tca tca ctc ttc agt gtg atc aca gtt gtt ggt gct gtg tat tgc      343
Leu Ser Ser Leu Phe Ser Val Ile Thr Val Val Gly Ala Val Tyr Cys
                90                  95                 100 atg ttg gta tca ctc cag gct ctc ttg gaa gga cct cta att tgt aat      391
Met Leu Val Ser Leu Gln Ala Leu Leu Glu Gly Pro Leu Ile Cys Asn
                105                 110                 115 act cag gcc aac agt act gtc act tgt gaa ttt tca ttg aaa aac tta      439
Thr Gln Ala Asn Ser Thr Val Thr Cys Glu Phe Ser Leu Lys Asn Leu
            120                 125                 130 agt aaa ttt gat cct gaa tcc ttc aat ctg ctg tgg ttc ttc aat ggc      487
Ser Lys Phe Asp Pro Glu Ser Phe Asn Leu Leu Trp Phe Phe Asn Gly
135                 140                 145 act tgt gtt tct cct act gat ttt aaa aac ccc acc atc aat aac atg      535
Thr Cys Val Ser Pro Thr Asp Phe Lys Asn Pro Thr Ile Asn Asn Met
150                 155                 160                 165 gtc agt aac tgg aaa ata ccc aac tcc aac tct gaa gaa gac aga cac      583
Val Ser Asn Trp Lys Ile Pro Asn Ser Asn Ser Glu Glu Asp Arg His
                170                 175                 180 agg att ttc cac ttc tca gta ttt atg agt ctc ctg ctt gtt gga atc      631
Arg Ile Phe His Phe Ser Val Phe Met Ser Leu Leu Leu Val Gly Ile
            185                 190                 195 ctg gag ctc ctg ttt ggg ctc agt cag ata ctc att ggt ttc ctt ggc      679
Leu Glu Leu Leu Phe Gly Leu Ser Gln Ile Leu Ile Gly Phe Leu Gly
            200                 205                 210 tgt ctg tgt ggc gtc tct cag cga cgg agt caa att gta taa              721
Cys Leu Cys Gly Val Ser Gln Arg Arg Ser Gln Ile Val
215                 220                 225 agggcaataa actagaatat cagtactttg aataatttga aaattgcatt taaaatatat    781
acttttgtaa gttcaataat gaagcatctt ctagaacaca gagtcatttt agtgcaaaca    841
gatgttttta gaatcatctc tgaagcaact ctcaaaaaaa aaattaacct atcaagctgg    901
gcagggctgg tacaggcctt cgatcccagc actcaggagc agaggctgga ggattcgag     961
tttgaggcct gcctagttta caaatgccaa gacagccagg actatacaga gaagctaaag   1021
cagaggactg catgaactc gcactagcgc gtcctgtatg tgcagtgcac ctccactccg    1081
gggggagaag ttaccagtgg gtgacacagg ggagaagcat aggaaagctt ttaggtttct   1141
tttttcctat gtatgccaaa agaacaattg tccacctcat cggttacaga agtatgtgtc   1201
ttagttttaa gaaatatata ttatgtgttt tgggaggaag accatgtttt aaaaatactt   1261
```

```
tacoctcaaa gccaaagtga tggaaaaatg ctgtgtttaa ctgacaggca catggcaatt    1321
catcatactc tattcttta tgtttgtatc tcttcatgat atctgctaag actttgggga    1381
aaaaaaatca gcctttaga agctggtttt tatgtatgct gatctttaaa agataggtaa    1441
caaaatgtat ttattgtatt aaaatgttat gaaatagaaa aactaaaaa tctacaattt    1501 tctg                                                                 1505

<210> SEQ ID NO 3
<211> LENGTH: 226
<212> TYPE: PRT
<213> ORGANISM: Mouse

<400> SEQUENCE: 3

Met Thr Cys Cys Glu Gly Trp Thr Ser Cys Asn Gly Phe Ser Leu Leu
1               5                   10                  15

Ile Leu Ile Leu Leu Gly Val Val Ile Asn Cys Ile Pro Leu Gly Ile
            20                  25                  30

Ser Leu Val Glu Ala Asp Ser Thr Ser Gln Asn Pro Ile Ser Cys Tyr
        35                  40                  45

Glu Trp Trp Phe Pro Gly Ile Ile Gly Ala Gly Leu Met Ala Ile Pro
    50                  55                  60

Ala Thr Thr Met Ser Leu Ala Ala Arg Lys Arg Ala Cys Cys Asn Asn
65                  70                  75                  80

Lys Thr Gly Met Phe Leu Ser Ser Leu Phe Ser Val Ile Thr Val Val
                85                  90                  95

Gly Ala Val Tyr Cys Met Leu Val Ser Leu Gln Ala Leu Leu Glu Gly
            100                 105                 110

Pro Leu Ile Cys Asn Thr Gln Ala Asn Ser Thr Val Thr Cys Glu Phe
        115                 120                 125

Ser Leu Lys Asn Leu Ser Lys Phe Asp Pro Glu Ser Phe Asn Leu Leu
    130                 135                 140

Trp Phe Phe Asn Gly Thr Cys Val Ser Pro Thr Asp Phe Lys Asn Pro
145                 150                 155                 160

Thr Ile Asn Asn Met Val Ser Asn Trp Lys Ile Pro Asn Ser Asn Ser
                165                 170                 175

Glu Glu Asp Arg His Arg Ile Phe His Phe Ser Val Phe Met Ser Leu
            180                 185                 190

Leu Leu Val Gly Ile Leu Glu Leu Leu Phe Gly Leu Ser Gln Ile Leu
        195                 200                 205

Ile Gly Phe Leu Gly Cys Leu Cys Gly Val Ser Gln Arg Arg Ser Gln
    210                 215                 220

Ile Val
225

<210> SEQ ID NO 4
<211> LENGTH: 2308
<212> TYPE: DNA
<213> ORGANISM: Human

<400> SEQUENCE: 4
aagccacttt gacaacgttt ctgagccagg ggtgaccatg acctgctgcg aaggatggac     60
atcctgcaat ggattcagcc tgctggttct actgctgtta ggagtagttc tcaatgtgat    120
acctctaatt gtcagcttag ttgaggaaga ccaatttct caaaacccca tctcttgctt    180
tgagtggtgg ttcccaggaa ttataggagc aggtctgatg gccattccag caacaacaat    240
```

```
gtccttgaca gcaagaaaaa gagcgtgctg caacaacaga actggaatgt ttctttcatc      300
acttttcagt gtgatcacag tcattggtgc tctgtattgc atgctgatat ccatccaggc      360
tctcttaaaa ggtcctctca tgtgtaattc tccaagcaac agtaatgcca attgtgaatt      420
ttcattgaaa acatcagtg acattcatcc agaatccttc aacttgcagt ggttttcaa        480
tgactcttgt gcacctccta ctggtttcaa taaacccacc agtaacgaca ccatggcgag      540
tggctggaga gcatctagtt tccacttcga ttctgaagaa acaaacata ggcttatcca       600
cttctcagta ttttaggtc tattgcttgt tggaattctg gaggtcctgt ttgggctcag       660
tcagatagtc atcggtttcc ttggctgtct gtgtggagtc tctaagcgaa gaagtcaaat     720
tgtgtagttt aatgggaata aaatgtaagt atcagtagtt tgaattaatt tgagaagtac     780
acttgttttc aaagtcatct ttgagatgat ttaaaaaatc aacccttcac gtagaaagca     840
cgttgtaaat gcataacact ctcatatcag tggttgattt gggaaaggtg agagaatt       900
tcaattagtt ttgtgttgta ctattcaaat ttttacctc ttcactgtgt gtagagaaag      960
gagaagggaa ggaggatgag aaggaacgga agtcatcctg aaaataaaag tacaggactt    1020
ttttttttt tttttgagac agggtctcaa aaaaggctgg agtacagtag tacagtggtg     1080
ctatctcagc ttactgcagc ctcaacctcc tgggctcagg tgattctccc atctcagcct    1140
ccctagtagc tgggactaca ggtgcgtgcc actatgccaa gctaatttt gtattttag      1200
tagagatggg ggttttccat attgcccagg ctggtcccga actcatggac tcaagtgatc    1260
tgcctgcctc agcctcctaa agtgctgcga ttacaggcat gagccatcgc gcctaaagga    1320
caggaccttt ttattgtatt tctttaaaga ataaatacat aacctgaatg caatcaagtc    1380
tttagatcta attctcagct tgcagggaac actaggacaa atccaaaaag tgggtcagcg    1440
ggcacagaat ggcccaattt tcaacaggaa aatgttataa agaaaaata ttttgaggg      1500
aactgttata gattaagaga atagaggcat gtttcagcta aacacatgta aactttgtca    1560
gagataattg ggaggagtat gtagaagaat cggattattg ttaattttgg taggtctgat    1620
aatggtttta tagtataaag gctgagtacc ccttatccaa aatgattaag atcagaagtg    1680
ttttggcttt cacatttttt tggatttggg aattttgcct ataataatga gacatcttgg    1740
ggatgggatg caagtctaac cacaaaattc atttatgtct catacacact ttgaacacct    1800
ggcctgaagg taatttcaca caatatttta aataactttg tgcatgaaac acaatttga    1860
ctgcattttg actgcaactc atcacatgag gtcaggtatg gaattttcca cttgtggtgt    1920
tacgttactg gctcaaaaag ttttggatct cggagcattc tggattttga attttggat    1980
tagtgatgct caacctgtat acagaaatgt cctcattttt aaaaaaagaa atgcatattt    2040
atatgtttta aaattacttc aaccaaaagc aacggggaga tgtttactgt tatatttagg    2100
tgacaggtac atggcaattc attatacccct cctatttcc tatgtttaca ttattcatta    2160
attaaaaaac aataacctaga aaacccaag actttcaaaa gctatttct atatgtgcca    2220
atctttaaaa acaggataa caagggtatt tatcacatta aaatgttgta aaacagcaaa    2280
gctaaaatct aaaaaaaaaa aaaaaaa                                        2308
```

<210> SEQ ID NO 5
<211> LENGTH: 2308
<212> TYPE: DNA
<213> ORGANISM: Human
<220> FEATURE:
<221> NAME/KEY: CDS
<222> LOCATION: (38)..(727)
<223> OTHER INFORMATION: coding sequence for insulin secretion inducer

```
<400> SEQUENCE: 5
aagccacttt gacaacgttt ctgagccagg ggtgacc atg acc tgc tgc gaa gga      55
                                        Met Thr Cys Cys Glu Gly
                                        1               5 tgg aca tcc tgc aat gga ttc agc ctg ctg gtt cta ctg ctg tta gga      103
Trp Thr Ser Cys Asn Gly Phe Ser Leu Leu Val Leu Leu Leu Leu Gly
            10                  15                  20 gta gtt ctc aat gtg ata cct cta att gtc agc tta gtt gag gaa gac      151
Val Val Leu Asn Val Ile Pro Leu Ile Val Ser Leu Val Glu Glu Asp
                25                  30                  35 caa ttt tct caa aac ccc atc tct tgc ttt gag tgg tgg ttc cca gga      199
Gln Phe Ser Gln Asn Pro Ile Ser Cys Phe Glu Trp Trp Phe Pro Gly
        40                  45                  50 att ata gga gca ggt ctg atg gcc att cca gca aca aca atg tcc ttg      247
Ile Ile Gly Ala Gly Leu Met Ala Ile Pro Ala Thr Thr Met Ser Leu
55                  60                  65                  70 aca gca aga aaa aga gcg tgc tgc aac aac aga act gga atg ttt ctt      295
Thr Ala Arg Lys Arg Ala Cys Cys Asn Asn Arg Thr Gly Met Phe Leu
                75                  80                  85 tca tca ctt ttc agt gtg atc aca gtc att ggt gct ctg tat tgc atg      343
Ser Ser Leu Phe Ser Val Ile Thr Val Ile Gly Ala Leu Tyr Cys Met
            90                  95                  100 ctg ata tcc atc cag gct ctc tta aaa ggt cct ctc atg tgt aat tct      391
Leu Ile Ser Ile Gln Ala Leu Leu Lys Gly Pro Leu Met Cys Asn Ser
        105                 110                 115 cca agc aac agt aat gcc aat tgt gaa ttt tca ttg aaa aac atc agt      439
Pro Ser Asn Ser Asn Ala Asn Cys Glu Phe Ser Leu Lys Asn Ile Ser
    120                 125                 130 gac att cat cca gaa tcc ttc aac ttg cag tgg ttt ttc aat gac tct      487
Asp Ile His Pro Glu Ser Phe Asn Leu Gln Trp Phe Phe Asn Asp Ser
135                 140                 145                 150 tgt gca cct cct act ggt ttc aat aaa ccc acc agt aac gac acc atg      535
Cys Ala Pro Pro Thr Gly Phe Asn Lys Pro Thr Ser Asn Asp Thr Met
                155                 160                 165 gcg agt ggc tgg aga gca tct agt ttc cac ttc gat tct gaa gaa aac      583
Ala Ser Gly Trp Arg Ala Ser Ser Phe His Phe Asp Ser Glu Glu Asn
            170                 175                 180 aaa cat agg ctt atc cac ttc tca gta ttt tta ggt cta ttg ctt gtt      631
Lys His Arg Leu Ile His Phe Ser Val Phe Leu Gly Leu Leu Leu Val
        185                 190                 195 gga att ctg gag gtc ctg ttt ggg ctc agt cag ata gtc atc ggt ttc      679
Gly Ile Leu Glu Val Leu Phe Gly Leu Ser Gln Ile Val Ile Gly Phe
    200                 205                 210 ctt ggc tgt ctg tgt gga gtc tct aag cga aga agt caa att gtg tag      727
Leu Gly Cys Leu Cys Gly Val Ser Lys Arg Arg Ser Gln Ile Val
215                 220                 225 tttaatggga ataaaatgta agtatcagta gtttgaatta atttgagaag tacacttgtt     787
ttcaaagtca tctttgagat gatttaaaaa atcaacccct cacgtagaaa gcacgttgta     847
aatgcataac actctcatat cagtggttga tttgggaaag gtggagagaa ttttcaatta     907
gttttgtgtt gtactattca aattttttac ctcttcactg tgtgtagaga aaggagaagg     967
gaaggaggat gagaaggaac ggaagtcatc ctgaaaataa aagtacagga cttttttttt    1027
tttttttga  dacagggtct caaaaaaggc tggagtacag tagtacagtg gtgctatctc    1087
agcttactgc agcctcaacc tcctgggctc aggtgattct cccatctcag cctccctagt    1147
agctgggact acaggtgcgt gccactatgc caagctaatt tttgtatttt tagtagagat    1207
gggggttttc catattgccc aggctggtcc cgaactcatg gactcaagtg atctgcctgc    1267
```

-continued

```
ctcagcctcc taaagtgctg cgattacagg catgagccat cgcgcctaaa ggacaggacc    1327
tttttattgt atttctttaa agaataaata cataacctga atgcaatcaa gtctttagat    1387
ctaattctca gcttgcaggg aacactagga caaatccaaa aagtgggtca gcgggcacag    1447
aatggcccaa ttttcaacag gaaaatgtta taaaagaaaa atattttga gggaactgtt     1507
atagattaag agaatagagg catgtttcag ctaaacacat gtaaactttg tcagagataa    1567
ttgggaggag tatgtagaag aatcggatta ttgttaattt tggtaggtct gataatggtt    1627
ttatagtata aaggctgagt accccttatc caaaatgatt aagatcagaa gtgttttggc    1687
tttcacattt ttttggattt tggaattttg cctataataa tgagacatct tggggatggg    1747
atgcaagtct aaccacaaaa ttcatttatg tctcatacac actttgaaca cctggcctga    1807
aggtaatttc acacaatatt ttaaataact ttgtgcatga aacacaattt tgactgcatt    1867
ttgactgcaa ctcatcacat gaggtcaggt atggaatttt ccacttgtgg tgttacgtta    1927
ctggctcaaa aagttttgga tctcggagca ttctggattt tgaattttg gattagtgat     1987
gctcaacctg tatacagaaa tgtcctcatt tttaaaaaaa gaaatgcata tttatatgtt    2047
ttaaaattac ttcaaccaaa agcaacgggg agatgtttac tgttatattt aggtgacagg    2107
tacatggcaa ttcattatac cctcctattt tcctatgttt acattattca ttaattaaaa    2167
aacaatacct agaaaaaccc aagactttca aaagctatt tctatatgtg ccaatcttta     2227
aaaaacagga taacaagggt attatcaca ttaaaatgtt gtaaaacagc aaagctaaaa     2287
tctaaaaaaa aaaaaaaaaa a                                              2308
```

<210> SEQ ID NO 6
<211> LENGTH: 229
<212> TYPE: PRT
<213> ORGANISM: Human

<400> SEQUENCE: 6

```
Met Thr Cys Cys Glu Gly Trp Thr Ser Cys Asn Gly Phe Ser Leu Leu
1               5                   10                  15

Val Leu Leu Leu Gly Val Val Leu Asn Val Ile Pro Leu Ile Val
            20                  25                  30

Ser Leu Val Glu Glu Asp Gln Phe Ser Gln Asn Pro Ile Ser Cys Phe
        35                  40                  45

Glu Trp Trp Phe Pro Gly Ile Ile Gly Ala Gly Leu Met Ala Ile Pro
    50                  55                  60

Ala Thr Thr Met Ser Leu Thr Ala Arg Lys Arg Ala Cys Cys Asn Asn
65                  70                  75                  80

Arg Thr Gly Met Phe Leu Ser Ser Leu Phe Ser Val Ile Thr Val Ile
                85                  90                  95

Gly Ala Leu Tyr Cys Met Leu Ile Ser Ile Gln Ala Leu Leu Lys Gly
            100                 105                 110

Pro Leu Met Cys Asn Ser Pro Ser Asn Ser Asn Ala Asn Cys Glu Phe
        115                 120                 125

Ser Leu Lys Asn Ile Ser Asp Ile His Pro Glu Ser Phe Asn Leu Gln
    130                 135                 140

Trp Phe Phe Asn Asp Ser Cys Ala Pro Pro Thr Gly Phe Asn Lys Pro
145                 150                 155                 160

Thr Ser Asn Asp Thr Met Ala Ser Gly Trp Arg Ala Ser Ser Phe His
                165                 170                 175

Phe Asp Ser Glu Glu Asn Lys His Arg Leu Ile His Pro Ser Val Phe
            180                 185                 190
```

-continued

```
Leu Gly Leu Leu Leu Val Gly Ile Leu Glu Val Leu Phe Gly Leu Ser
    195                 200                 205

Gln Ile Val Ile Gly Phe Leu Gly Cys Leu Cys Gly Val Ser Lys Arg
    210                 215                 220

Arg Ser Gln Ile Val
225

<210> SEQ ID NO 7
<211> LENGTH: 2308
<212> TYPE: DNA
<213> ORGANISM: Human

<400> SEQUENCE: 7
aagccacttt gacaacgttt ctgagccagg ggtgaccatg acctgctgcg aaggatggac      60
atcctgcaat ggattcagcc tgctggttct actgctgtta ggagtagttc tcaatgcgat     120
acctctaatt gtcagcttag ttgaggaaga ccaatttttct caaaaccca tctcttgctt     180 tgagtggtgg ttcccaggaa ttataggagc aggtctgatg ccattccag caacaacaat     240 gtccttgaca gcaagaaaaa gagcgtgctg caacaacaga actggaatgt ttctttcatc     300
acttttcagt gtgatcacag tcattggtgc tctgtattgc atgctgatat ccatccaggc     360
tctcttaaaa ggtcctctca tgtgtaattc tccaagcaac agtaatgcca attgtgaatt     420
ttcattgaaa aacatcagtg acattcatcc agaatccttc aacttgcagt ggttttttcaa     480 tgactcttgt gcacctccta ctggtttcaa taaacccacc agtaacgaca ccatggcgag     540
tggctggaga gcatctagtt tccacttcga ttctgaagaa acaaacata ggcttatcca     600 cttctcagta ttttttaggtc tattgcttgt tggaattctg gaggtcctgt ttgggctcag     660
tcagatagtc atcggtttcc ttggctgtct gtgtggagtc tctaagcgaa gaagtcaaat     720
tgtgtagttt aatgggaata aaatgtaagt atcagtagtt tgaattaatt tgagaagtac     780
acttgttttc aaagtcatct ttgagatgat ttaaaaaatc aacccttcac gtagaaagca     840
cgttgtaaat gcataacact ctcatatcag tggttgattt gggaaaggtg agagaatttt     900
tcaattagtt ttgtgttgta ctattcaaat ttttttacctc ttcactgtgt gtagagaaag     960
gagaagggaa ggaggatgag aaggaacgga agtcatcctg aaaataaaag tacaggactt    1020 ttttttttt tttttgagac agggtctcaa aaaaggctgg agtacagtag tacagtggtg    1080
ctatctcagc ttactgcagc ctcaacctcc tgggctcagg tgattctccc atctcagcct    1140
ccctagtagc tgggactaca ggtgcgtgcc actatgccaa gctaattttt gtatttttag    1200
tagagatggg ggttttccat attgcccagg ctggtcccga actcatggac tcaagtgatc    1260
tgcctgcctc agcctcctaa agtgctgcga ttacaggcat gagccatcgc gcctaaagga    1320
caggaccttt ttattgtatt tctttaaaga ataaatacat aacctgaatg caatcaagtc    1380
tttagatcta attctcagct tgcagggaac actaggacaa atccaaaaag tgggtcagcg    1440
ggcacagaat ggcccaattt tcaacaggaa aatgttataa agaaaaata ttttgaggg    1500 aactgttata gattaagaga atagaggcat gtttcagcta aacacatgta aactttgtca    1560
gagataattg ggaggagtat gtagaagaat cggattattg ttaattttgg taggtctgat    1620
aatggtttta tagtataaag gctgagtacc ccttatccaa aatgattaag atcagaagtg    1680
ttttggcttt cacattttt tggattttgg aattttgcct ataataatga acatcttgg    1740 ggatgggatg caagtctaac cacaaaattc atttatgtct catacacact ttgaacacct    1800
ggcctgaagg taatttcaca caatatttta aataactttg tgcatgaaac acaattttga    1860
ctgcattttg actgcaactc atcacatgag gtcaggtatg gaattttcca cttgtggtgt    1920
```

-continued

```
tacgttactg gctcaaaaag ttttggatct cggagcattc tggattttga attttttggat    1980 tagtgatgct caacctgtat acagaaatgt cctcattttt aaaaaaagaa atgcatattt     2040
atatgtttta aaattacttc aaccaaaagc aacggggaga tgtttactgt tatatttagg    2100
tgacaggtac atggcaattc attataccct cctatttttcc tatgtttaca ttattcatta    2160
attaaaaaac aataacctaga aaacccaag actttcaaaa gctattttct atatgtgcca    2220
atctttaaaa aacaggataa caagggtatt tatcacatta aaatgttgta aaacagcaaa    2280
gctaaaatct aaaaaaaaaa aaaaaaaa                                        2308
```

<210> SEQ ID NO 8
<211> LENGTH: 2308
<212> TYPE: DNA
<213> ORGANISM: Human
<220> FEATURE:
<221> NAME/KEY: CDS
<222> LOCATION: (38)..(727)
<223> OTHER INFORMATION: coding sequence for insulin secretion inducer

<400> SEQUENCE: 8

```
aagccacttt gacaacgttt ctgagccagg ggtgacc atg acc tgc tgc gaa gga          55
                                        Met Thr Cys Cys Glu Gly
                                         1               5 tgg aca tcc tgc aat gga ttc agc ctg ctg gtt cta ctg ctt tta gga         103
Trp Thr Ser Cys Asn Gly Phe Ser Leu Leu Val Leu Leu Leu Leu Gly
            10                  15                  20 gta gtt ctc aat gcg ata cct cta att gtc agc tta gtt gag gaa gac         151
Val Val Leu Asn Ala Ile Pro Leu Ile Val Ser Leu Val Glu Glu Asp
        25                  30                  35 caa ttt tct caa aac ccc atc tct tgc ttt gag tgg tgg ttc cca gga         199
Gln Phe Ser Gln Asn Pro Ile Ser Cys Phe Glu Trp Trp Phe Pro Gly
    40                  45                  50 att ata gga gca ggt ctg atg gcc att cca gca aca aca atg tcc ttg         247
Ile Ile Gly Ala Gly Leu Met Ala Ile Pro Ala Thr Thr Met Ser Leu
55                  60                  65                  70 aca gca aga aaa aga gcg tgc tgc aac aac aga act gga atg ttt ctt         295
Thr Ala Arg Lys Arg Ala Cys Cys Asn Asn Arg Thr Gly Met Phe Leu
                75                  80                  85 tca tca ctt ttc agt gtg atc aca gtc att ggt gct ctg tat tgc atg         343
Ser Ser Leu Phe Ser Val Ile Thr Val Ile Gly Ala Leu Tyr Cys Met
            90                  95                 100 ctg ata tcc atc cag gct ctc tta aaa ggt cct ctc atg tgt aat tct         391
Leu Ile Ser Ile Gln Ala Leu Leu Lys Gly Pro Leu Met Cys Asn Ser
        105                 110                 115 cca agc aac agt aat gcc aat tgt gaa ttt tca ttg aaa aac atc agt         439
Pro Ser Asn Ser Asn Ala Asn Cys Glu Phe Ser Leu Lys Asn Ile Ser
    120                 125                 130 gac att cat cca gaa tcc ttc aac ttg cag tgg ttt ttc aat gac tct         487
Asp Ile His Pro Glu Ser Phe Asn Leu Gln Trp Phe Phe Asn Asp Ser
135                 140                 145                 150 tgt gca cct cct act ggt ttc aat aaa ccc acc agt aac gac acc atg         535
Cys Ala Pro Pro Thr Gly Phe Asn Lys Pro Thr Ser Asn Asp Thr Met
                155                 160                 165 gcg agt ggc tgg aga gca tct agt ttc cac ttc gat tct gaa gaa aac         583
Ala Ser Gly Trp Arg Ala Ser Ser Phe His Phe Asp Ser Glu Glu Asn
            170                 175                 180 aaa cat agg ctt atc cac ttc tca gta ttt tta ggt cta ttg ctt gtt         631
Lys His Arg Leu Ile His Phe Ser Val Phe Leu Gly Leu Leu Leu Val
        185                 190                 195 gga att ctg gag gtc ctg ttt ggg ctc agt cag ata gtc atc ggt ttc         679
Gly Ile Leu Glu Val Leu Phe Gly Leu Ser Gln Ile Val Ile Gly Phe
```

-continued

```
Gly Ile Leu Glu Val Leu Phe Gly Leu Ser Gln Ile Val Ile Gly Phe
         200                 205                 210 ctt ggc tgt ctg tgt gga gtc tct aag cga aga agt caa att gtg tag      727
Leu Gly Cys Leu Cys Gly Val Ser Lys Arg Arg Ser Gln Ile Val
215                 220                 225 tttaatggga ataaaatgta agtatcagta gtttgaatta atttgagaag tacacttgtt    787
ttcaaagtca tctttgagat gatttaaaaa atcaaccctt cacgtagaaa gcacgttgta    847
aatgcataac actctcatat cagtggttga tttgggaaag gtggagagaa ttttcaatta    907
gttttgtgtt gtactattca aattttttac ctcttcactg tgtgtagaga aggagaagg     967
gaaggaggat gagaaggaac ggaagtcatc ctgaaaataa aagtacagga cttttttttt   1027
tttttttttga dacagggtct caaaaaaggc tggagtacag tagtacagtg gtgctatctc  1087
agcttactgc agcctcaacc tcctgggctc aggtgattct cccatctcag cctccctagt   1147
agctgggact acaggtgcgt gccactatgc caagctaatt tttgtatttt tagtagagat   1207
gggggttttc catattgccc aggctggtcc cgaactcatg gactcaagtg atctgcctgc   1267
ctcagcctcc taaagtgctg cgattacagg catgagccat cgcgcctaaa ggacaggacc   1327
ttttttattgt atttctttaa agaataaata cataacctga atgcaatcaa gtctttagat  1387
ctaattctca gcttgcaggg aacactagga caaatccaaa aagtgggtca gcgggcacag   1447
aatggcccaa ttttcaacag gaaaatgtta taaaagaaaa atattttttga gggaactgtt  1507
atagattaag agaatagagg catgtttcag ctaaacacat gtaaactttg tcagagataa   1567
ttgggaggag tatgtagaag aatcggatta ttgttaattt tggtaggtct gataatggtt   1627
ttatagtata aaggctgagt accccttatc caaaatgatt aagatcagaa gtgttttggc   1687
tttcacatttt ttttggattt tggaattttg cctataataa tgagacatct tggggatggg  1747
atgcaagtct aaccacaaaa ttcatttatg tctcatacac actttgaaca cctggcctga   1807
aggtaatttc acacaatatt ttaaataact ttgtgcatga aacacaattt tgactgcatt   1867
ttgactgcaa ctcatcacat gaggtcaggt atggaattt ccacttgtgg tgttacgtta    1927
ctggctcaaa aagttttgga tctcggagca ttctggattt tgaattttg gattagtgat    1987
gctcaacctg tatacagaaa tgtcctcatt tttaaaaaaa gaaatgcata tttatatgtt   2047
ttaaaattac ttcaaccaaa agcaacgggg agatgtttac tgtttatattt aggtgacagg  2107
tacatggcaa ttcattatac cctcctatttt tcctatgttt acattattca ttaattaaaa  2167
aacaatacct agaaaaaccc aagactttca aaagctatttt tctatatgtg ccaatctttta 2227
aaaaacagga taacaagggt atttatcaca ttaaaatgtt gtaaaacagc aaagctaaaa   2287
tctaaaaaaa aaaaaaaaaa a                                              2308
```

<210> SEQ ID NO 9
<211> LENGTH: 229
<212> TYPE: PRT
<213> ORGANISM: Human

<400> SEQUENCE: 9

```
Met Thr Cys Cys Glu Gly Trp Thr Ser Cys Asn Gly Phe Ser Leu Leu
1               5                   10                  15

Val Leu Leu Leu Leu Gly Val Val Leu Asn Ala Ile Pro Leu Ile Val
            20                  25                  30

Ser Leu Val Glu Glu Asp Gln Phe Ser Gln Asn Pro Ile Ser Cys Phe
        35                  40                  45

Glu Trp Trp Phe Pro Gly Ile Ile Gly Ala Gly Leu Met Ala Ile Pro
    50                  55                  60
```

```
Ala Thr Thr Met Ser Leu Thr Ala Arg Lys Arg Ala Cys Cys Asn Asn
 65                  70                  75                  80

Arg Thr Gly Met Phe Leu Ser Ser Leu Phe Ser Val Ile Thr Val Ile
                 85                  90                  95

Gly Ala Leu Tyr Cys Met Leu Ile Ser Ile Gln Ala Leu Leu Lys Gly
            100                 105                 110

Pro Leu Met Cys Asn Ser Pro Ser Asn Ser Asn Ala Asn Cys Glu Phe
        115                 120                 125

Ser Leu Lys Asn Ile Ser Asp Ile His Pro Glu Ser Phe Asn Leu Gln
    130                 135                 140

Trp Phe Phe Asn Asp Ser Cys Ala Pro Pro Thr Gly Phe Asn Lys Pro
145                 150                 155                 160

Thr Ser Asn Asp Thr Met Ala Ser Gly Trp Arg Ala Ser Ser Phe His
                165                 170                 175

Phe Asp Ser Glu Glu Asn Lys His Arg Leu Ile His Phe Ser Val Phe
            180                 185                 190

Leu Gly Leu Leu Leu Val Gly Ile Leu Glu Val Leu Phe Gly Leu Ser
        195                 200                 205

Gln Ile Val Ile Gly Phe Leu Gly Cys Leu Cys Gly Val Ser Lys Arg
    210                 215                 220

Arg Ser Gln Ile Val
225

<210> SEQ ID NO 10
<211> LENGTH: 19
<212> TYPE: PRT
<213> ORGANISM: Human

<400> SEQUENCE: 10

Ala Leu Tyr Cys Met Leu Ile Ser Ile Gln Ala Leu Leu Lys Gly Pro
1               5                  10                  15

Leu Met Cys

<210> SEQ ID NO 11
<211> LENGTH: 19
<212> TYPE: PRT
<213> ORGANISM: Human

<400> SEQUENCE: 11

Cys Asn Asn Arg Thr Gly Met Phe Leu Ser Ser Leu Phe Ser Val Ile
1               5                  10                  15

Thr Val Ile

<210> SEQ ID NO 12
<211> LENGTH: 19
<212> TYPE: PRT
<213> ORGANISM: Human

<400> SEQUENCE: 12

Thr Ser Asn Asp Thr Met Ala Ser Gly Trp Arg Ala Ser Ser Phe His
1               5                  10                  15

Phe Asp Ser
```

METHOD OF TREATMENT OF DIABESTES OR REDUCTION IN PANCREATIC BETA-CELLS

TECHNICAL FIELD

The present invention relates to an insulin secretion inducer, insulin secretion-inducing composition and a method of manufacturing the same, an accelerator for increasing the number of pancreatic β-cells, a composition for increasing the number of pancreatic β-cells and a method of manufacturing same, in addition to a virus vector for genetic treatment, for use primarily in the treatment of diabetes and of various other diseases.

BACKGROUND ART

In recent years, the alimentary tract has attracted attention not only for absorbing nutrients during meals but also as an internal secretory organ producing gastrointestinal hormones. In addition to ghrelin produced by the stomach, Gastric inhibitory polypeptide: GIP or Glucagon-like peptide-1: GLP-1 secreted from the small intestine have been cloned. Ghrelin has a food intake stimulatory effect and is related to energy metabolism. GLP-1 and GIP are termed incretins and act on pancreatic β-cells in response to food load to induce insulin secretion. GIP is also expressed in adipose tissue and the fact that a GIP-receptor knockout mouse does not experience an increase in body weight even when given high fat foods suggests a connection with obesity.

Thus gastrointestinal hormones are related to energy metabolism and food intake behavior and elucidation of their function is assisting in the development of methods of treating various diseases primarily diabetes. However an overall description of gastrointestinal hormones is not yet clear and many facets remain elusive.

DISCLOSURE OF THE INVENTION

Problems to be Solved by the Invention

Thus the present invention has the object of searching for genes encoding unknown polypeptides from the alimentary tract in order to provide new medicinal uses based on such identified genes.

Means for Solving the Problems

The present inventors have conducted diligent research with respect to the above point and by using an SST method (Signal Sequence Trap Method: Nat. Biotechnol. 1999 May; 17(5): 487-90. A signal sequence trap based on a constitutively active cytokine receptor. Kojima T, Kitamura T.), the present inventors have discovered that a clone CF266 (mCF266) identified using a cDNA fragment isolated from the murine alimentary tract is specifically expressed in the alimentary tract, that there is an insulin secretion effect in a culture supernatant of cells transfected with mCF266 and that mCF266 displays an insulin secretion effect when mCF266 is forcibly expressed in vivo by using a forced expression system employing an adenovirus vector. The present inventors have discovered that the same action is displayed by a synthetic polypeptide which is a fragment of a polypeptide having an amino acid sequence encoded by human CF266 (hCF266) which corresponds to mCF266.

Furthermore the present inventors have discovered that hCF266 has an action of increasing the number of pancreatic β-cell when hCF266 is forcibly expressed in vivo by using a forced expression system employing an adenovirus vector and that the number of pancreatic β-cells is increased in mCF266 transgenic mice. Furthermore the present inventors have discovered the same action is displayed by a synthetic polypeptide which is a fragment of a polypeptide having an amino acid sequence encoded by hCF266. Although the factor causing the increase in the number of pancreatic β-cells is thought to be either a propagation accelerator for pancreatic β-cells or a degradation inhibitor for pancreatic β-cells, in the present specification, both are referred to globally as "accelerator for increasing the number of pancreatic β-cells".

The present invention was completed using the above insights.

The insulin secretion inducer includes at least one of the following active ingredients (a) to (c):

(a) a polypeptide having an amino acid sequence encoded by DNA having a base sequence as set forth in SEQ. ID. No. 1 or SEQ. ID. No. 4;

(b) a polypeptide having an insulin secretion inducing action and having an amino acid sequence in which one or several amino acids have been substituted, deleted and/or added to an amino acid sequence encoded by DNA having a base sequence as set forth in SEQ. ID. No. 1 or SEQ. ID. No. 4; and (c) a fragment of the polypeptide in (a) or (b) having an insulin secretion inducing action.

The insulin secretion inducer according to the present invention is characterized in that a polypeptide having an insulin secretion inducing action and having an amino acid sequence in which one or several amino acids have been substituted, deleted and/or added to an amino acid sequence encoded by DNA having a base sequence as set forth in SEQ. ID. No. 4, is a polypeptide having an amino acid sequence encoded by DNA having a base sequence as set forth in SEQ. ID. No. 7.

The insulin secretion inducer according to the present invention includes at least one of the following active ingredients (d) to (f):

(d) a polypeptide having an amino acid sequence as set forth in SEQ. ID. No. 3 or SEQ. ID. No. 6;

(e) a polypeptide having an insulin secretion inducing action and having an amino acid sequence in which one or several amino acids have been substituted, deleted and/or added to an amino acid sequence as set forth in SEQ. ID. No. 3 or SEQ. ID. No. 6; and (f) a fragment of the polypeptide in (d) or (e) having an insulin secretion inducing action.

The insulin secretion inducer according to the present invention is characterized in that the polypeptide having the insulin secretion inducing action and having the amino acid sequence in which one or several amino acids have been substituted, deleted and/or added to an amino acid sequence as set forth in SEQ. ID. No. 6, is a polypeptide having an amino acid sequence as set forth in SEQ. ID. No. 9.

The insulin secretion inducer according to the present invention is characterized in that the fragment of the polypeptide in (d) or (e) having the insulin secretion inducing action is a polypeptide including an amino acid sequence in SEQ. ID. No. 10, SEQ. ID. No. 11 or SEQ. ID. No. 12.

The present invention provides use of at least one of the following (a) to (c) in the preparation of an insulin secretion inducer:

(a) a polypeptide having an amino acid sequence encoded by DNA having a base sequence as set forth in SEQ. ID. No. 1 or SEQ. ID. No. 4;

(b) a polypeptide having an insulin secretion inducing action and having an amino acid sequence in which one or several amino acids have been substituted, deleted and/or added to an amino acid sequence encoded by DNA having a base sequence as set forth in SEQ. ID. No. 1 or SEQ. ID. No. 4; and (c) a fragment of the polypeptide in (a) or (b) having an insulin secretion inducing action.

The present invention provides use of at least one of the following (d) to (f) in the preparation of an insulin secretion inducer:

(d) a polypeptide having an amino acid sequence as set forth in SEQ. ID. No. 3 or SEQ. ID. No. 6;

(e) a polypeptide having an insulin secretion inducing action and having an amino acid sequence in which one or several amino acids have been substituted, deleted and/or added to an amino acid sequence as set forth in SEQ. ID. No. 3 or SEQ. ID. No. 6; and (f) a fragment of the polypeptide in (d) or (e) having an insulin secretion inducing action.

The insulin secretion-inducing composition according to the present invention includes at least one active ingredient being a polypeptide having an amino acid sequence as set forth in SEQ. ID. No. 3, a polypeptide having an amino acid sequence as set forth in SEQ. ID. No. 6, a polypeptide having an amino acid sequence as set forth in SEQ. ID. No. 9, a polypeptide including an amino acid sequence as set forth in SEQ. ID. No. 10, a polypeptide including an amino acid sequence as set forth in SEQ. ID. No. 11 or a polypeptide including an amino acid sequence as set forth in SEQ. ID. No. 12.

A method of preparing an insulin secretion-inducing composition, the method including the steps of integrating DNA as an exogenous gene into culturable cells, the DNA being DNA having a base sequence as set forth in at least one of SEQ. ID. No. 1, SEQ. ID. No. 4 and SEQ. ID. No. 7, or being DNA capable of hybridizing under stringent conditions with a strand complementary to DNA having the base sequence as set forth in at least one of SEQ. ID. No. 1, SEQ. ID. No. 4 and SEQ. ID. No. 7, culturing the cells and expressing the gene.

The viral vector employed for inducing insulin secretion according to the genetic treatment of the present invention is characterized in that DNA is integrated as an exogenous gene into a viral vector enabling expression of the exogenous gene, the DNA being DNA having a base sequence as set forth in at least one of SEQ. ID. No. 1, SEQ. ID. No. 4 and SEQ. ID. No. 7, or being DNA capable of hybridizing under stringent conditions with a strand complementary to DNA having the base sequence as set forth in at least one of SEQ. ID. No. 1, SEQ. ID. No. 4 and SEQ. ID. No. 7.

The viral vector inducing insulin secretion according to the genetic treatment of the present invention is characterized in that it is an adenovirus vector.

An accelerator for increasing the number of pancreatic β-cells according to the present invention includes at least one of the following active ingredients (a) to (c):

(a) a polypeptide having an amino acid sequence encoded by DNA having a base sequence as set forth in SEQ. ID. No. 1 or SEQ. ID. No. 4;

(b) a polypeptide having an action of increasing the number of pancreatic β-cells and having an amino acid sequence in which one or several amino acids have been substituted, deleted and/or added to an amino acid sequence encoded by DNA having a base sequence as set forth in SEQ. ID. No. 1 or SEQ. ID. No. 4; and (c) a fragment of the polypeptide in (a) or (b) having an action of increasing the number of pancreatic β-cells.

The accelerator for increasing the number of pancreatic β-cells according to the present invention is characterized in that the polypeptide having the action of increasing the number of pancreatic β-cells and having the amino acid sequence in which one or a plurality of amino acids has been substituted, deleted and/or added to the amino acid sequence encoded by DNA having the base sequence as set forth in SEQ. ID. No. 4, is a polypeptide having an amino acid sequence encoded by DNA having a base sequence as set forth in SEQ. ID. No. 7.

The accelerator for increasing the number of pancreatic β-cells according to the present invention includes at least one of the following active ingredients (d) to (f):

(d) a polypeptide having an amino acid sequence as set forth in SEQ. ID. No. 3 or SEQ. ID. No. 6;

(e) a polypeptide having an action of increasing the number of pancreatic β-cells and having an amino acid sequence in which one or several amino acids have been substituted, deleted and/or added to an amino acid sequence as set forth in SEQ. ID. No. 3 or SEQ. ID. No. 6; and (f) a fragment of the polypeptide in (d) or (e) having an action of increasing the number of pancreatic β-cells.

The accelerator for increasing the number of pancreatic β-cells according to the present invention is characterized in that the polypeptide having an action of increasing the number of pancreatic β-cells and having the amino acid sequence in which one or several amino acids have been substituted, deleted and/or added to the amino acid sequence as set forth in SEQ. ID. No. 6, is a polypeptide having an amino acid sequence as set forth in SEQ. ID. No. 9.

The accelerator for increasing the number of pancreatic β-cells according to the present invention is characterized in that a fragment of the polypeptide in (d) or (e) having the action of increasing the number of pancreatic β-cells is a polypeptide including an amino acid sequence as set forth in SEQ. ID. No. 10, SEQ. ID. No. 11 or SEQ. ID. No. 12.

The present invention provides use of at least one of the following (a) to (c) in the preparation of an accelerator for increasing the number of pancreatic β-cells:

(a) a polypeptide having an amino acid sequence encoded by DNA having a base sequence as set forth in SEQ. ID. No. 1 or SEQ. ID. No. 4;

(b) a polypeptide having an action of increasing the number of pancreatic β-cells and having an amino acid sequence in which one or several amino acids have been substituted, deleted and/or added to an amino acid sequence encoded by DNA having a base sequence as set forth in SEQ. ID. No. 1 or SEQ. ID. No. 4; and (c) a fragment of the polypeptide in (a) or (b) having an action of increasing the number of pancreatic β-cells.

The present invention provides use of at least one of the following (d) to (f) in the preparation of an accelerator for increasing the number of pancreatic β-cells:

(d) a polypeptide having an amino acid sequence having a base sequence as set forth in SEQ. ID. No. 3 or SEQ. ID. No. 6;

(e) a polypeptide having an action of increasing the number of pancreatic β-cells and having an amino acid sequence in which one or several amino acids have been substituted, deleted and/or added to an amino acid sequence as set forth in SEQ. ID. No. 3 or SEQ. ID. No. 6; and (f) a fragment of the polypeptide in (d) or (e) having an action of increasing the number of pancreatic β-cells.

A composition for increasing the number of pancreatic β-cells according to the present invention includes at least one active ingredient being a polypeptide having an amino acid sequence as set forth in SEQ. ID. No. 3, a polypeptide having an amino acid sequence as set forth in SEQ. ID. No. 6, a polypeptide having an amino acid sequence as set forth in SEQ. ID. No. 9, a polypeptide including an amino acid sequence as set forth in SEQ. ID. No. 10, a polypeptide including an amino acid sequence as set forth in SEQ. ID. No. 11 or a polypeptide including an amino acid sequence as set forth in SEQ. ID. No. 12.

A method of preparing a composition for increasing the number of pancreatic β-cells according to the present invention includes the steps of integrating DNA as an exogenous gene into culturable cells, the DNA being DNA having a base sequence as set forth in at least one of SEQ. ID. No. 1, SEQ. ID. No. 4 and SEQ. ID. No. 7, or being DNA capable of hybridizing under stringent conditions with a strand complementary to DNA having the base sequence as set forth in at least one of SEQ. ID. No. 1, SEQ. ID. No. 4 and SEQ. ID. No. 7, culturing the cells and expressing the gene.

A viral vector for increasing the number of pancreatic β-cells according to the genetic treatment of the present invention is characterized in that DNA is integrated as an exogenous gene into a viral vector enabling expression of the exogenous gene, the DNA being DNA having a base sequence as set forth in at least one of SEQ. ID. No. 1, SEQ. ID. No. 4 and SEQ. ID. No. 7, or being DNA capable of hybridizing under stringent conditions with a strand complementary to DNA having the base sequence as set forth in at least one of SEQ. ID. No. 1, SEQ. ID. No. 4 and SEQ. ID. No. 7.

The viral vector for increasing the number of pancreatic β-cells according to the genetic treatment of the present invention is characterized in that it is an adenovirus vector.

Effects of the Invention

According to the present invention, an insulin secretion inducer, insulin secretion-inducing composition and a method of manufacturing the same, an accelerator for increasing the number of pancreatic β-cells, a composition for increasing the number of pancreatic β-cells and a method of manufacturing same, and a virus vector for genetic treatment, for use primarily in the treatment of diabetes, and of various other diseases are provided.

PREFERRED MODE FOR CARRYING OUT THE INVENTION

Figure 1:
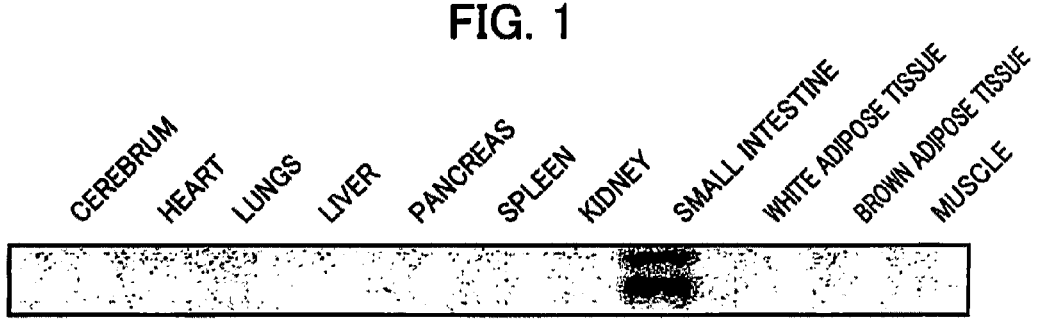
FIG. 1 is a northern blot showing a distribution of expression of mCF266, using mCF266 cDNA as a probe.

The insulin secretion inducer according to the present invention includes at least one of the following active ingredients (a) to (c):

(a) a polypeptide having an amino acid sequence encoded by DNA having a base sequence as set forth in SEQ. ID. No. 1 or SEQ. ID. No. 4;

(b) a polypeptide having an insulin secretion inducing action and having an amino acid sequence in which one or several amino acids has been substituted, deleted and/or added to an amino acid sequence encoded by DNA having a base sequence as set forth in SEQ. ID. No. 1 or SEQ. ID. No. 4; and (c) a fragment of the polypeptide in (a) or (b) having an insulin secretion inducing action.

The accelerator for increasing the number of pancreatic β-cells according to the present invention includes at least one of the following active ingredients (a) to (c):

(a) a polypeptide having an amino acid sequence encoded by DNA having a base sequence as set forth in SEQ. ID. No. 1 or SEQ. ID. No. 4;

(b) a polypeptide having an action of increasing the number of pancreatic β-cells and having an amino acid sequence in which one or several amino acids have been substituted, deleted and/or added to an amino acid sequence encoded by DNA having a base sequence as set forth in SEQ. ID. No. 1 or SEQ. ID. No. 4; and (c) a fragment of the polypeptide in (a) or (b) having an action of increasing the number of pancreatic β-cells.

mCF266 acquired from a murine alimentary tract by the present inventors is DNA having the base sequence as set forth in SEQ. ID. No. 1. This DNA has a known overall length of 1505 bp and is DNA encoding a membrane protein Tm4sf20 (Transmembrane 4L six family member 20) expressed in murine muscle tissue (NCBI: LOCUS NM 025453). The protein coding sequence (CDS) of mCF266 is 41 . . . 721 and encodes a polypeptide having a 266 amino acid sequence as set forth in SEQ. ID. No. 3 (refer to SEQ. ID. No. 2). However, there have been no reports to date of this polypeptide having an insulin secretion inducing action or action of increasing the number of pancreatic β-cells.

Furthermore the present inventors have confirmed that human CF266 (hCF266) which corresponds to mCF266 has the same action as mCF266. hCF266 is DNA having the base sequence as set forth in SEQ. ID. No. 4 and has a known length of 2308 bp as DNA encoding human TM4SF20 (NCBI: LOCUS NM 024795). The CDS of hCF266 is 38 . . . 727 and encodes a polypeptide having a 229 amino acid sequence as set forth in SEQ. ID. No. 6 (refer to SEQ. ID. No. 5). However there have been no reports to date of this polypeptide having an insulin secretion inducing action or action of increasing the number of pancreatic β-cells.

The insulin secretion inducer and accelerator for increasing the number of pancreatic β-cells according to the present invention have an active ingredient being a polypeptide having an amino acid sequence encoded by DNA having a base sequence as set forth in SEQ. ID. No. 1 or SEQ. ID. No. 4.

As long as an insulin secretion inducing action and an action for increasing the number of pancreatic β-cells is present, the insulin secretion inducer and accelerator for increasing the number of pancreatic β-cells according to the present invention may also include an active ingredient being a polypeptide having an amino acid sequence in which one or several amino acids have been substituted, deleted and/or added to an amino acid sequence of the polypeptide above. It is known that a polypeptide having an amino acid sequence modified by substitution, deletion and/or addition of one or several amino acids from a given amino acid sequence may retain its physiological activity (Mark, D. F. et al., Proc. Natl. Acad. Sci. USA (1984) 81, 5662-5666, Zoller, M. J. & Smith, M. Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413).

When one or several amino acids are substituted by another amino acid, it is desirable that the properties of the amino acid side chains before and after substitution are conserved. The properties of amino acid side chains include hydrophobic amino acids (A, I, L, M, F, P, W, Y, V), hydrophilic amino acids (R, D, N, C, E, Q, G, H, K, S T), amino acids having aliphatic side chains (G, A, V, L, I, P), amino acids having side chains containing hydroxyl groups (S, T, V), amino acids having side chains containing sulfur atoms (C, M), amino acids having side chains containing amides (D, N, E, Q), amino acids having side chains containing bases (R, K, H) and amino acids having side chains containing aromatic series (H, F, Y, W) (the letters in the brackets represent single letter symbols for amino acids).

More precisely, a polypeptide having an insulin secretion inducing action and an action of increasing the number of pancreatic β-cells and having an amino acid sequence in which one or several amino acids have been substituted, deleted and/or added to an amino acid sequence encoded by DNA having a base sequence as set forth in SEQ. ID. No. 4 for example includes a polypeptide having a 229 amino acid base sequence as set forth in SEQ. ID. No. 9 which is encoded by DNA having a base sequence as set forth in SEQ. ID. No. 7 based on a single nucleotide polymorphism (SNPs) of hCF266 (refer to SEQ. ID. No. 8). The difference between the polypeptide having the amino acid sequence set forth in SEQ. ID. No. 6 and polypeptide having the amino acid sequence set forth in SEQ. ID. No. 9 is that the 27.sup.th amino acid in the former is valine (hCF266(27V)) whereas the latter has alanine (hCF266(27A)).

As long as an insulin secretion inducing action and an action of increasing the number of pancreatic β-cells is present, the insulin secretion inducer and the accelerator for increasing the number of pancreatic β-cells according to the present invention may include an active ingredient being a fragment of the above polypeptides.

More precisely, a fragment of a polypeptide having an insulin secretion inducing action and an action of increasing the number of pancreatic β-cells for example includes a polypeptide including at least a 19 amino acid sequence ALYCMLISIQALLKGPLMC (refer to SEQ. ID. No. 10) corresponding to the 98-116$^{th}$ amino acids of the polypeptide having the amino acid sequence as set forth in SEQ. ID. No. 6, a polypeptide including at least a 19 amino acid sequence CNNTRGMFLSSLFSVITVI (refer to SEQ. ID. No. 11) corresponding to the 78-96$^{th}$ amino acids of the same polypeptide or a polypeptide including at least a 19 amino acid sequence TSNDTMASGWRASSFHFDS (refer to SEQ. ID. No. 12) corresponding to the 161-179$^{th}$ amino acids of the same polypeptide.

The polypeptide having an insulin secretion inducing action and action of increasing the number of pancreatic β-cells or a fragment of such a polypeptide may be produced by chemical synthesis or may be obtained using recombinant technologies. For example the polypeptide may be obtained from a culture supernatant by incorporating DNA having a base sequence as set forth in SEQ. ID. No. 1, SEQ. ID. No. 4 or SEQ. ID. No. 7, or DNA capable of hybridizing under stringent conditions with a strand complementary to DNA having the base sequence as set forth in SEQ. ID. No. 1, SEQ. ID. No. 4 or SEQ. ID. No. 7 as an exogenous gene into a culturable host cell and culturing the cell in order to enable genetic expression.

The host cell may be a suitable known cell such as a bacterium, yeast cell, insect cell or animal cell. Animal cells include HEK293 cells, HEK293T cells, CHO-K1 cells and COS cells.

Herein the term "DNA capable of hybridizing under stringent conditions" means DNA obtained by using the object DNA as a probe and employing a method including colony hybridization, plaque hybridization or southern blot hybridization. For example, DNA and the like may be identified by using a filter fixing DNA originating from a colony or plaque, and in the presence of 0.7-1.0 M sodium chloride, hybridization is performed at 65° C. Thereafter, 0.1-2×SSC solution (1×SSC composition: 150 mM sodium chloride, 15 mM sodium citrate) is used to wash the filter under conditions of 65° C. (if necessary, refer to Molecular Cloning: A Laboratory Manual, 2$^{nd}$, Ed., Cold Spring Harbor Laboratory, Cold Spring Harbor, N.Y., 1989. or similar text). Homology between the base sequence of DNA used as a probe and the base sequence of DNA capable of hybridizing under stringent conditions is preferably at least 80%, more preferably at least 90%, still more preferably at least 93%, particularly preferably at least 95% and most preferably at least 98%.

The separation and purification of the polypeptide or fragment thereof may be performed using methods normally used in peptide chemistry including for example ion-exchange resin, partition chromatography, gel chromatography, and reverse phase chromatography.

The insulin secretion inducer and accelerator for increasing the number of pancreatic β-cells according to the present invention may be administered as an injectable preparation (subcutaneously, intracutaneously, intramuscularly, intravenously, intraperitoneally or the like), as a preparation administered transdermally, transmucosally, or pernasally or as a preparation administered orally (tablet, capsule, granules, liquid, suspension or the like). In response to the requirements of a method of administration or form of preparation, the insulin secretion inducer and accelerator for increasing the number of pancreatic β-cells according to the present invention may include suitable additives such as suspending agents, solubilization agent, stabilizers, tonicity agents, preserving agents, absorption preventing agents, surface active agents, dilution agents, excipients, pH adjusting agents and anti-oxidizing agents. The method and used amounts may be suitably determined with respect to the gender, age, body weight and malady of a patient.

For example, the polypeptide being the active ingredient, or a fragment thereof, may as required be converted to a pharmaceutically acceptable alkali metal salt such as sodium salt, organic salt such as an acetate or inorganic salt such as a hydrochloride and may be formed as a pharmaceutical formulation in the form of a freeze-dried article after sterilization. During use, induction of insulin secretion and acceleration of an increase in pancreatic β-cells are enabled by intravenous administration in an injectable form by dissolution into saline or the like.

The polypeptide being the active ingredient, or the fragment thereof, of an insulin secretion inducer or an accelerator for increasing the number of pancreatic β-cells according to the present invention may be used alone as a pure substance purified to a high degree or may be a mixture of a plurality of types of substances and may be used in various aspects as an insulin secretion inducer composition or a composition for increasing the number of pancreatic β-cells.

A viral vector for inducing insulin secretion or a viral vector for increasing the number of pancreatic β-cells in accordance with the genetic therapy of the present invention is characterized by incorporating DNA having a base sequence set forth in at least one of SEQ. ID. No. 1, SEQ. ID. No. 4 and SEQ. ID. No. 7, or DNA capable of hybridizing under stringent conditions with a strand complementary to DNA having the base sequence as set forth in at least one of SEQ. ID. No. 1, SEQ. ID. No. 4 and SEQ. ID. No. 7 as an exogenous gene in a viral vector enabling expression of the exogenous gene. An actual example of a viral vector includes an adenovirus vector constructed by linking DNA having a base sequence as set forth in any one of SEQ. ID. No. 1, SEQ. ID. No. 4 and SEQ. ID. No. 7 with a CAG promoter. This type of viral vector for example enables induction of insulin secretion and increase in the number of pancreatic β-cells by intravenous injection for example.

Since the insulin secretion inducer, insulin secretion inducer composition and the viral vector for inducing insulin secretion by genetic therapy according to the present invention display an excellent insulin secretion action in vivo, it is effective for diseases associated with reduction of insulin secretion capability and in particular for treatment of type-2 diabetes. In other words, use of the insulin secretion inducer, insulin secretion inducer composition and the viral vector for inducing insulin secretion by genetic therapy provides a method of treatment for diseases associated with reduction of insulin secretion capability and in particular for treatment of type-2 diabetes.

Since the accelerator for increasing the number of pancreatic β-cells, composition for increasing the number of pancreatic β-cells and the viral vector for increasing the number of pancreatic β-cells by genetic therapy according to the present invention display an excellent action for increasing the number of pancreatic β-cells in vivo, it is effective for diseases associated with reduction or necrosis in pancreatic β-cells and in particular for treatment of type-1 diabetes. In other words, use of the accelerator for increasing the number of pancreatic β-cells, composition for increasing the number of pancreatic β-cells and the viral vector for increasing the number of pancreatic β-cells by genetic therapy provide a method of treatment for diseases associated with reduction or necrosis in pancreatic β-cells and in particular for treatment of type-1 diabetes.

EXAMPLES

The present invention will be described in further detail with reference to the embodiments. However interpretation of the present invention is not limited by the following description.

Reference Example 1

Site Expression Distribution of mCF266

In reference example 1, the distribution of expression by site of mRNA of mCF266 acquired from the alimentary tract of a mouse using an SST method was examined.

Firstly various organs and tissues (cerebrum, heart, lungs, liver, pancreas, spleen, kidney, small intestine, white adipose tissue, brown adipose tissue and muscle) were removed from a mouse and total RNA was extracted in accordance with the instruction manual attached to TRIzol (Invitrogen). Then hybridization was performed by preparing a membrane having 10 μg/lane according to a defined method and using a probe of cDNA (mRNA clone) formed from mCF266 labeled with [α-$^{32}$P] dCTP. The results are shown in FIG. 1. As clearly shown by FIG. 1, mCF266 is specifically expressed in the small intestine.

EMBODIMENT 1

Action of Culture Supernatant of CF266 Transfected Cells on Cultured Cell Strain MIN6 from Murine Pancreatic β-Cells In Embodiment 1, an action was confirmed with respect to MIN6 cells using a culture supernatant of a HEK293T cell strain originating from fetal kidney epithelial cells transfected with CF266.

Firstly, HEK293T cells subcultured in DMEM media enriched with 5% FCS and an antibiotic (penicillin 100 U/mL, streptomycin 10 mg/mL) were plated onto a 10 cm dish at a concentration of $1 \times 10^6$ cells/dish. On the following day, HEK292T cells were transfected with an expression vector for mCF266 (pCAGGS-mCF266) using a FuGENE6 (Roche) and mCF266 was forcibly expressed. After 24 hours, the media was exchanged for Opti-MEM media and after a further 24 hours, a culture supernatant was recovered.

Next, MIN6 cells subcultured in DMEM media (high glucose, Invitrogen) enriched with 15% FCS, an antibiotic (penicillin 100 U/mL, streptomycin 10 mg/mL) and 2-mercaptoethanol were plated onto a 24-well plate at a concentration of $3 \times 10^5$ cells/well. On the following day, 0.5 mL/well KRBH buffer solution (2.8 mM glucose) was added and pre-culturing was conducted for 30 minutes. Then 0.5 mL/well of a mixed solution of the above culture supernatant and KRBH buffer solution (1:1(v/v)) was added and stimulated for one hour. Then glucose-stimulated insulin secretion (GSIS) was measured for the MIN6 cells. The measurement was performed by measuring insulin in the culture solution using an ELISA method (using a REBIS Insulin Kit (Shibayagi): same hereafter). The insulin value was normalized using the total protein amount of MIN6 cells.

In the same manner, respective expression vectors for DNA (hCF266(27V)) having a base sequence as set forth in SEQ. ID. No. 4 cloned from a human alimentary tract cDNA library (BD Biosciences) and DNA (hCF266(27A)) having a base sequence as set forth in SEQ. ID. No. 7 acquired by using a known method to introduce a mutation into DNA (hCF266 (27V)) were transfected into HEK293T cells and subjected respectively to forcible expression. The culture supernatant was used to measure glucose-stimulated insulin secretion (GSIS) in MIN6 cells in the same manner as that described above.

Figure 2:
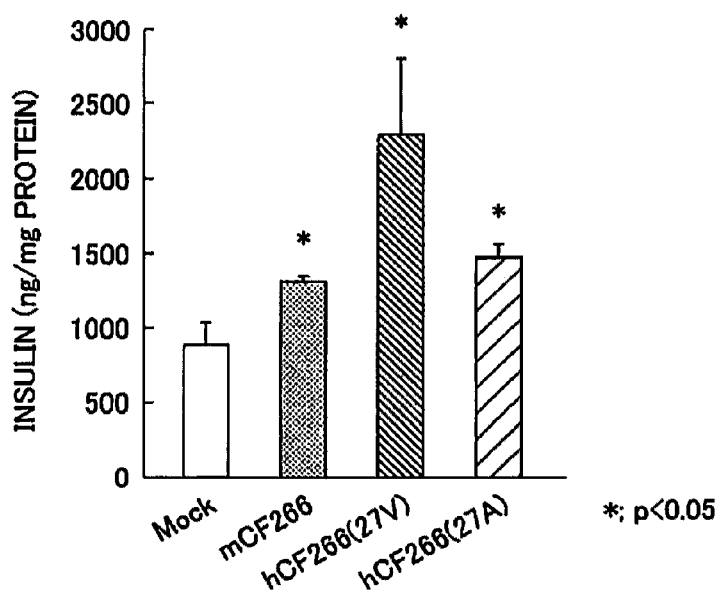
FIG. 2 is a graph showing induction of insulin secretion with respect to a culture cell line of murine pancreatic β-cells in a culture supernatant of cells transfected with CF266.

The results are shown in FIG. 2. In the figure, "Mock" shows the results when adding a culture supernatant obtained by using the same method as above to transfect an empty vector (pCAGGS) into HEK293T cells. As clearly shown by FIG. 2, the culture supernatant of cells forcibly expressing CF266 induce glucose-stimulated insulin secretion with respect to MIN6 cells and displays an excellent action when hCF266(27V) is forcibly expressed.

EMBODIMENT 2

Action of mCF266 with Respect to a Type-2 Diabetes Model KK/Ay Mouse

In the second embodiment, an adenoviral vector expressing mCF266 was used to confirm the action of mCF266 with respect to a KK/Ay mouse which is a type-2 diabetes model mouse.

Firstly an adenoviral vector (prepared using ViraPower which is a tradename of Invitrogen) constructed by linking mCF266 to a CAG promoter was intravenously injected at a concentration of $6 \times 10^9$ PFU/mL into the caudal vein of a 18-week old KK/Ay mouse (body weight approximately 47-51 g) given a high-fat high-sucrose diet. After four days, an intravenous glucose tolerance test (i.v. GTT) was performed by periodically taking blood and measuring the blood-glucose level of the serum and the insulin level.

Figure 3A:
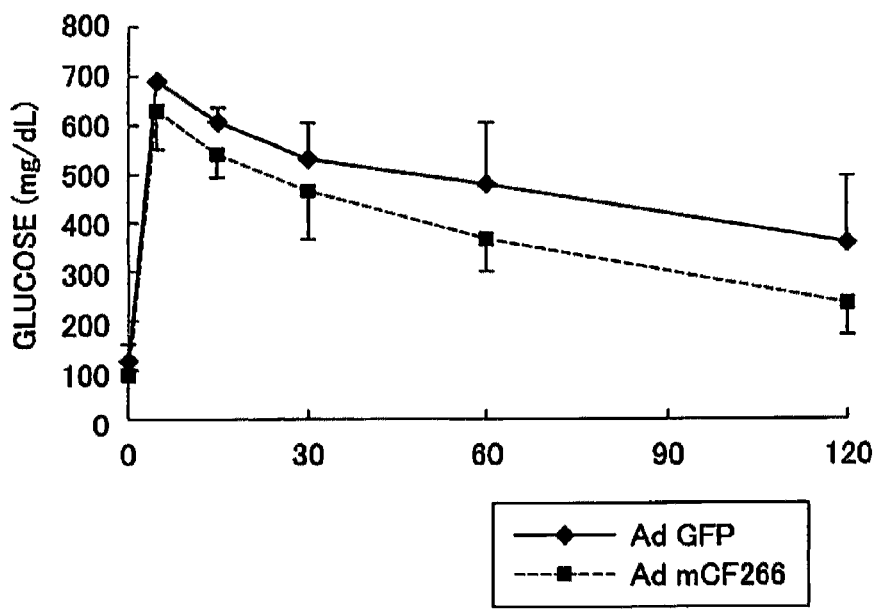
FIG. 3A and FIG. 3B are graphs showing induction of insulin secretion with respect to a model mouse for type-2 diabetes using a recombinant adenovirus expressing mCF266.
Figure 3B:
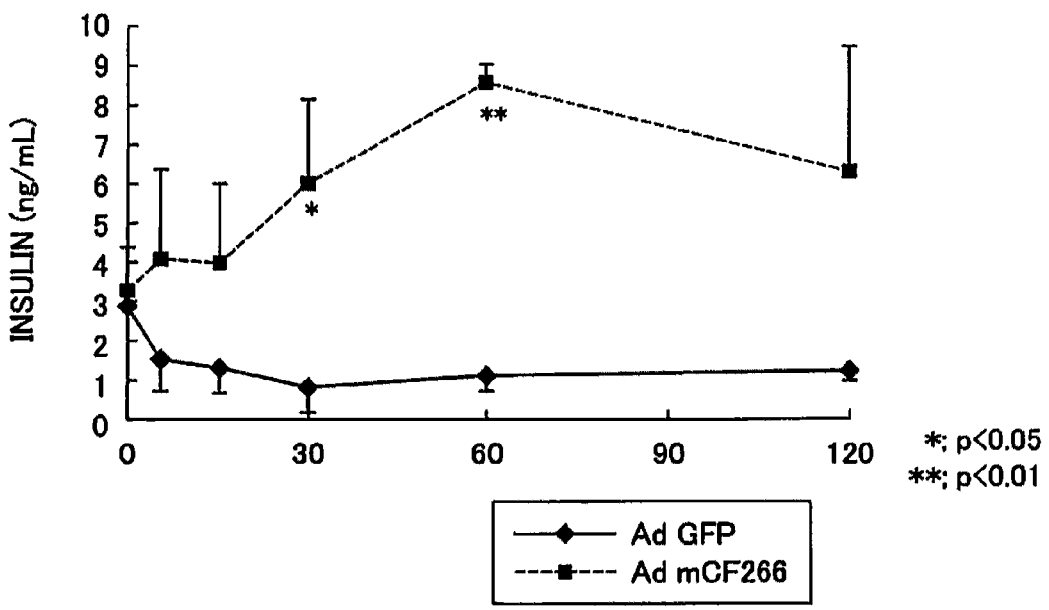

The results are shown in FIG. 3A and FIG. 3B. In the figures, "Ad GFP" shows the results when using an adenoviral vector constructed by linking DNA encoding GFP in place of mCF266. As clearly shown by FIG. 3A and FIG. 3B, when mCF266 is expressed in vivo in the type-2 diabetes model mouse, in comparison with the control expressing GFP, although the blood-glucose level displays only a slightly low tendency (FIG. 3A), the insulin value is significantly higher (FIG. 3B). Consequently expression of mCF266 is shown to induce insulin secretion.

EMBODIMENT 3

Action of Polypeptides Contained in Culture Supernatant of Cells Transfected with hCF266(27V) on Islets of Langerhans from Murine Pancreas In the third embodiment, a polypeptide contained in the culture supernatant of HEK293T cells transfected with hCF266(27V) was formed by chemical synthesis and the action of the synthetic polypeptide was confirmed with respect to islets of Langerhans from a murine pancreas.

Firstly, using the same method as the first embodiment, an expression vector for hCF266(27V) was transfected into HEK293T cells, hCF266(27V) was forcibly expressed and the culture supernatant recovered. Then an anion exchange column (POROS HQ column; ABI) was used to fractionate the recovered culture supernatant.

Next, islets of Langerhans from a pancreas isolated from a C57BL/6 mouse were plated into a 24-well plate at a concentration of 10 islets/well. After culturing for 2 hours in RPMI1640 media (10% FCS; Invitrogen), 0.5 mL/well of KRBH buffer solution (2.8 mM glucose or 20 mM glucose) was added and pre-culturing was performed for 30 minutes. Then 0.5 mL/well of a mixed solution of the above culture supernatant and KRBH buffer solution (1:1(v/v)) was added and stimulated for one hour. Then glucose-stimulated insulin secretion (GSIS) was measured for the islets of Langerhans from a murine pancreas. The measurement was performed by using an ELISA method to measure the insulin in the culture solution. The fractions confirmed to have insulin secretion inducing properties were analyzed using a mass spectrometer (TOF-MAS) and three types of polypeptides predicted to have a 19 amino acid sequence from a specifically observed peak mass were chemically synthesized. The three polypeptides are ALYCMLISIQALLKGPLMC (polypeptide A: refer to SEQ. ID. No. 10), CNNTRGMFLSSLFSVITVI (polypeptide B: refer to SEQ. ID. No. 11) and TSNDTMASGWRASSFHFDS (polypeptide C: refer to SEQ. ID. No. 12).

Then 0.5 mL/well of a solution dissolving the respective three polypeptides A-C in KRBH buffer solution at a concentration of 10 nM was added to islets of Langerhans from a murine pancreas pre-cultured for 30 minutes using the same method as above and then stimulated for 30 minutes. Then glucose-stimulated insulin secretion was measured for the islets of Langerhans from a murine pancreas using the same method as above. The insulin value was normalized using total DNA amount for the islets of Langerhans from a murine pancreas.

Figure 4:
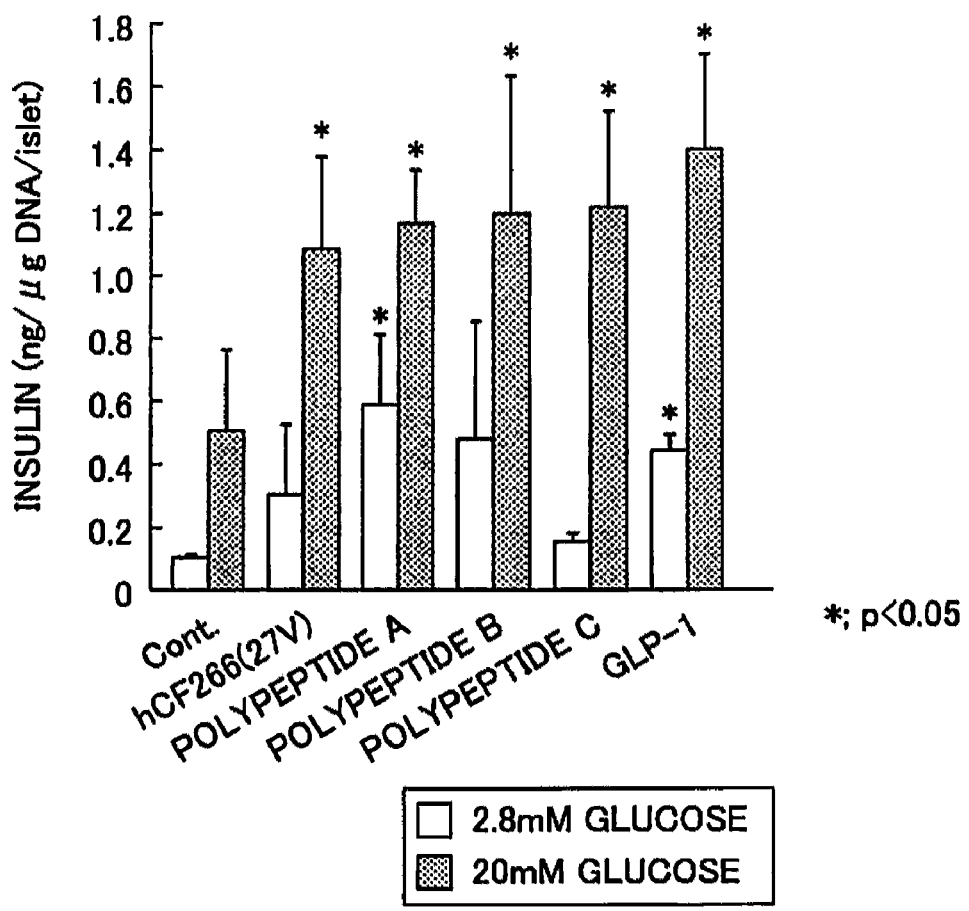
FIG. 4 is a graph showing induction of insulin secretion with respect to islets of Langerhans from a murine pancreas due to the action of a fragment of a polypeptide having an amino acid sequence encoded by hCF266(27V)

The results are shown in FIG. 4. In the figure, "Cont." shows the results of performing experiments using the method above in addition to stimulating by addition of only KRBH buffer solution. "hCF266(27V)" shows the results for experiments conducted using the same method as above in addition to causing stimulation by addition of a mixed solution of the above culture supernatant of HEK293T cells transfected with hCF266(27V) and KRBH buffer solution (1:1(v/v)). Furthermore "GLP-1" shows the results for experiments conducted using the same method as above in addition to causing stimulation by addition of a solution dissolving human GLP-1 (Peptide Institute Inc.) at a concentration of 10 nM in KRBH buffer solution. As clearly shown by FIG. 4, the three types of polypeptide A-C induce glucose-stimulated insulin secretion with respect to islets of Langerhans from a murine pancreas.

EMBODIMENT 4

Action of hCF266(27V) on a Type-1 Diabetes STZ Model Mouse

In the fourth embodiment, an adenoviral vector expressing hCF266(27V) was used to confirm the action of hCF266 (27V) with respect to an STZ model mouse which is a type-1 diabetes model mouse.

Firstly a 7-week old C57BL/6 mouse (body weight approximately 18-20 g) was fasted for 18 hours from day 0 and then streptozocin dissolved in saline (100 mg/kg body weight) was administered into the interperitoneal region and free feeding was immediately allowed. From the following day, after fasted for 18 hours the same amount of streptozocin was re-administered on the second day into the interperitoneal region and free feeding was immediately allowed. The serum blood-glucose level was measured on the seventh day. A fasting blood glucose level of greater than or equal to 150 mg/dL was determined to be diabetes and the experiment described hereafter was conducted. On the same day, a recombinant adenovirus (prepared using ViraPower which is a tradename of Invitrogen) constructed by linking hCF266 (27V) to a CAG promoter was intravenously injected at a concentration of $1 \times 10^9$ PFU/mL into the caudal vein of a STZ mouse determined to be suffering diabetes. On the twelfth day, an oral glucose tolerance test (OGTT) was performed by periodically taking blood and measuring the blood-glucose level of the serum and the insulin level.

Figure 5:
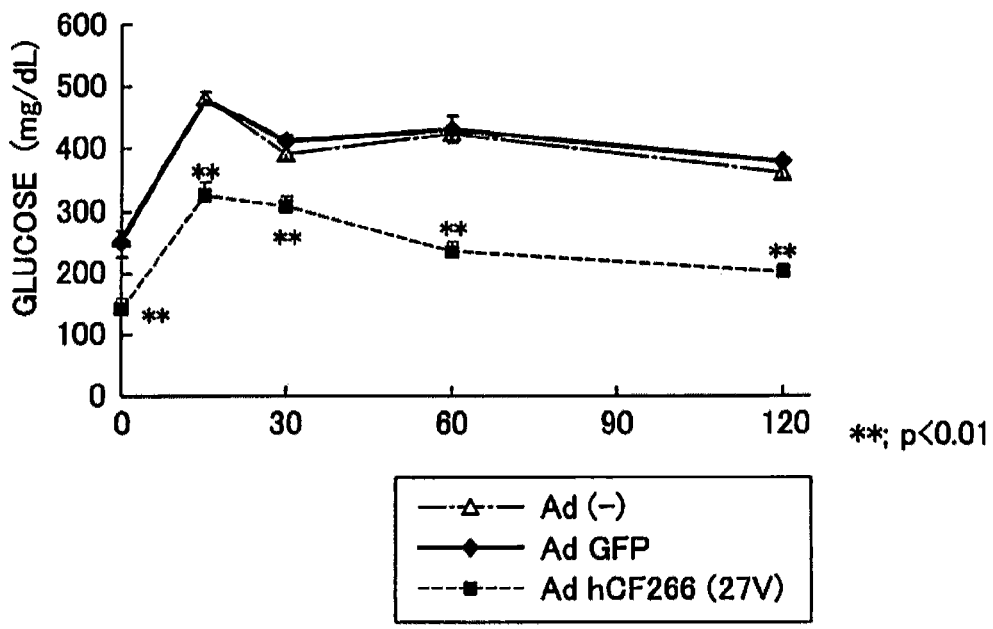
FIG. 5 is a graph showing reduction in blood glucose level with respect to a model mouse for type-1 diabetes using a recombinant adenovirus expressing hCF266(27V)

The results are shown in FIG. 5. In the figure, "Ad (−)" shows the results of using an adenoviral vector not incorporating an exogenous gene. "Ad GFP" shows the results of using an adenoviral vector constructed by linking DNA encoding GFP in place of hCF266(27V). As clearly shown by FIG. 5, when hCF266(27V) is expressed in vivo in the type-1 diabetes model mouse, in comparison with the control expressing GFP or expressing nothing, the blood glucose level is significantly reduced. Consequently expression of hCF266(27V) is shown to suppress increases in the blood glucose level.

The pancreas of the STZ mice was removed and after fixing the tissue with paraformaldehyde, the tissue sample preparation office at University of Tsukuba was employed to prepare a paraffin-embedded section. After the section was removed from paraffin, antigen activation was performed for 30 minutes at room temperature using 0.1% Triton X-100 and then blocking was performed for one hour at room temperature using 5% skim milk. After blocking, a primary antibody reaction was performed overnight at 4° C. using polyclonal anti-insulin guinea pig antibody (Daco) and polyclonal anti-glucagon rabbit antibody (Daco). The section was washed using Tris-buffered saline containing 0.1% Tween 20 (TBST). A secondary antibody reaction was performed in a darkroom for one hour at room temperature using polyclonal sheep anti-guinea pig IgG conjugated FITC antibody (Daco) and polyclonal goat anti-rabbit IgG conjugated Cy3 antibody (Daco). The section was washed using TBST. The section was thereafter mounted on a fluorescence photobleaching prevention agent (VECTASHILD Mounting Medium; Vector) and observed through a fluorescence microscope (BZ-8000; KEYENCE) to measure the surface ratio ($\beta$-cells/$\alpha$-cells) of $\beta$-cells to $\alpha$-cells.

Figure 6:
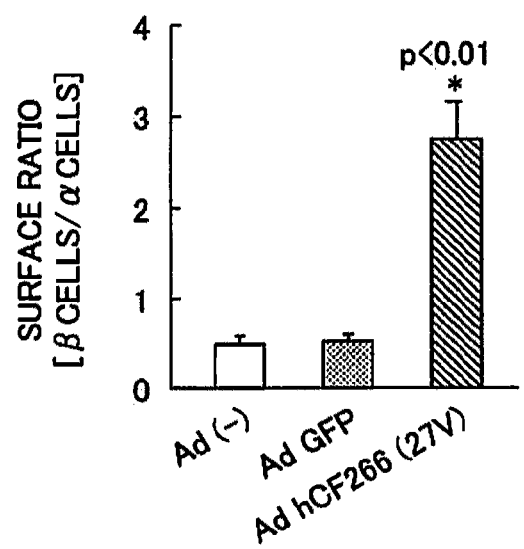
FIG. 6 is a graph showing an increase in the number of pancreatic β-cells with respect to a model mouse for type-1 diabetes using a recombinant adenovirus expressing hCF266 (27V)

The results are shown in FIG. 6. As clearly shown by FIG. 6, when hCF266(27V) is expressed in vivo in the type-1 diabetes model mouse, in comparison with the control expressing GFP or expressing nothing, the surface ratio ($\beta$-cells/$\alpha$-cells) of $\beta$ cells to $\alpha$ cells is significantly increased. Consequently expression of hCF266(27V) has been shown to increase the number of $\beta$-cells.

EMBODIMENT 5

Action of mCF266 in Transgenic Mice

In the fifth embodiment, the action of mCF266 in transgenic mice was confirmed.

Firstly, an mCF266 expression vector (pCAGGS-mCF266) was constructed by linking mCF266 to a CAG promoter and linearized. The University of Tsukuba Laboratory Animal Resource Center was employed to produce a transgenic mouse. The introduced gene was confirmed using PCR and southern blotting and mating for five generations with C57BL/6 mice was conducted.

The pancreas of the transgenic mice was removed and after fixing the tissue with paraformaldehyde, the tissue sample preparation office at University of Tsukuba was employed to prepare a paraffin-embedded section. After the section was removed from paraffin, antigen activation was performed for 30 minutes at room temperature using 0.1% Triton X-100 and then blocking was performed for one hour at room temperature using 5% skim milk. After blocking, a primary antibody reaction was performed overnight at 4° C. using polyclonal anti-insulin guinea pig antibody (Daco) and polyclonal anti-glucagon rabbit antibody (Daco). The section was washed using Tris-buffered saline containing 0.1% Tween20 (TBST). A secondary antibody reaction was performed in a darkroom for one hour at room temperature using polyclonal sheep anti-guinea pig IgG conjugated FITC antibody (Daco) and polyclonal goat anti-rabbit IgG conjugated Cy3 antibody (Daco). The section was washed using TBST. The section was thereafter mounted on a fluorescence photobleaching prevention agent (VECTASHILD Mounting Medium; Vector) and observed through a fluorescence microscope (BZ-8000; KEYENCE) to measure the surface area of islets of Langerhans stained by insulin relative to the pancreas surface area on the section. The number of islets of Langerhans was normalized with reference to a wild-type mouse taking a value of 1.

Figure 7A:
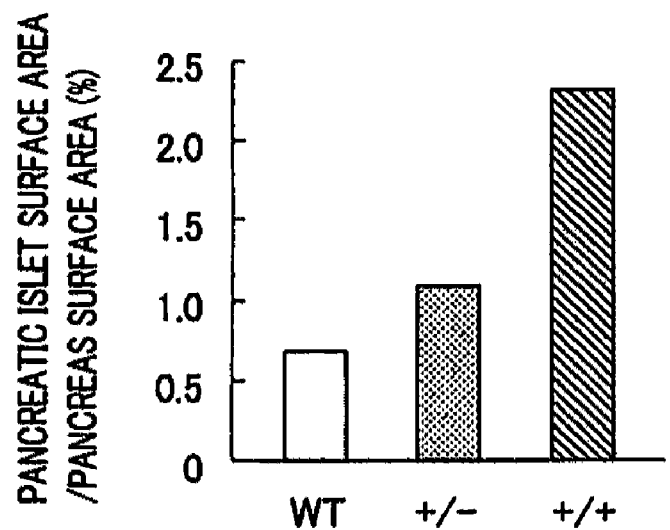
FIG. 7A and FIG. 7B are graphs showing an increase in the number and area of pancreatic β-cells by mCF266 using a transgenic mouse.
Figure 7B:
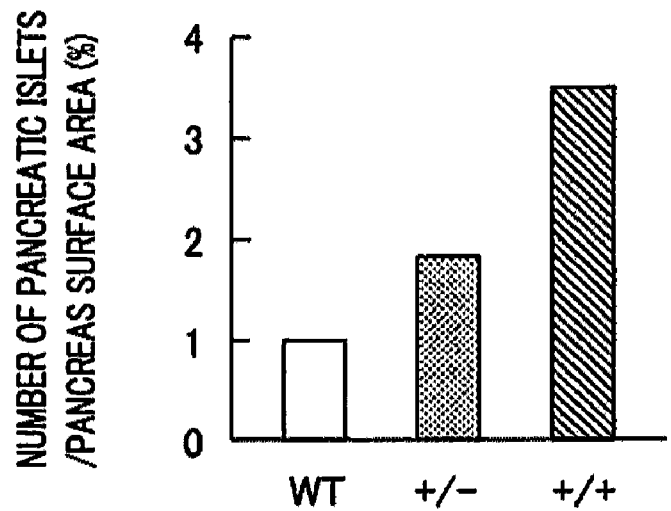

The results are shown in FIG. 7A and FIG. 7B. In the figures, "WT" shows the results when a wild-type mouse is used. As clearly shown by FIG. 7A and FIG. 7B, in comparison with a wild-type mouse, the surface area (FIG. 7A) and the number (FIG. 7B) of $\beta$-cells is conspicuously increased depending on whether the sample is hetero (+/−) or homo (+/+). Thus expression of mCF266 has been shown to increase the number of $\beta$-cells.

EMBODIMENT 6

Action of Polypeptide Contained in Culture Supernatant of hCF266(27V) Transfected Cells on Type-1 Diabetes STZ Model Mice In the sixth embodiment, the action of synthetic polypeptides A-C on Type-1 diabetes STZ model mice was confirmed in the same manner as the third embodiment.

Firstly a 7-week old C57BL/6 mouse (body weight approximately 18-20 g) was fasted for 18 hours from day 0 and then streptozocin dissolved in saline (100 mg/kg body weight) was fasted for 18 hours from day 0 and then streptozocin dissolved in saline (100 mg/kg body weight) was administered into the interperitoneal region and free feeding was immediately allowed. From the following day, after fasted for 18 hours the same amount of streptozocin was re-administered on the second day into the interperitoneal region and free feeding was immediately allowed. The serum blood-glucose level was measured on the seventh day. A fasting blood glucose level of greater than or equal to 150 mg/dL was determined as diabetes and the experiment described hereafter was conducted. STZ mice determined to have diabetes were administered into the interperitoneal region twice daily the polypeptide A-C (25 nmol/kg body weight) dissolved in saline for eight weeks from the seventh day.

The pancreas of the STZ mice was removed and after fixing the tissue with paraformaldehyde, the tissue sample preparation office at University of Tsukuba was employed to prepare a paraffin-embedded section. After the section was removed from paraffin, antigen activation was performed for 30 minutes at room temperature using 0.1% Triton X-100 and then blocking was performed for one hour at room temperature using 5% skim milk. After blocking, a primary antibody reaction was performed overnight at 4° C. using polyclonal anti-insulin guinea pig antibody (Daco) and polyclonal anti-glucagon rabbit antibody (Daco). The section was washed using Tris-buffered saline containing 0.1% Tween 20 (TBST). A secondary antibody reaction was performed in a darkroom for one hour at room temperature using polyclonal sheep anti-guinea pig IgG conjugated FITC antibody (Daco) and polyclonal goat anti-rabbit IgG conjugated Cy3 antibody (Daco). The section was washed using TBST. The section was thereafter mounted on a fluorescence photobleaching prevention agent (VECTASHILD Mounting Medium; Vector) and observed through a fluorescence microscope (BZ-8000; KEYENCE) to measure the surface ratio ($\beta$-cells/$\alpha$-cells) of $\beta$-cells to $\alpha$-cells.

Figure 8:
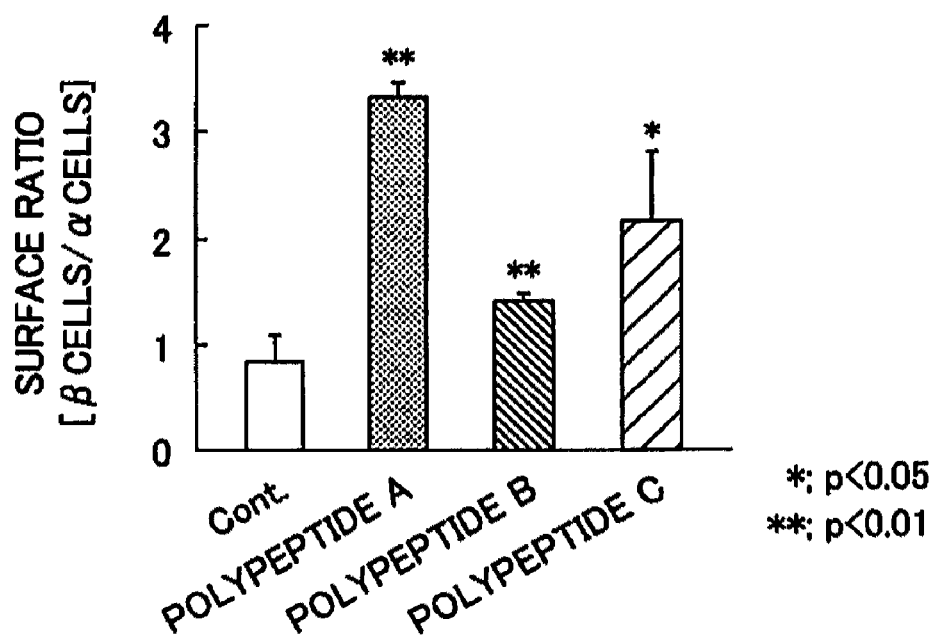
FIG. 8 is a graph showing an increase in the number of pancreatic β-cells with respect to a model mouse for type-1 diabetes due to the action of a fragment of a polypeptide having an amino acid sequence encoded by hCF266(27V).

The results are shown in FIG. 8. In the figures, "Cont." shows the results of an experiment conducted using the same method as that described above in addition to using physiological saline solution not containing the polypeptides A-C. As clearly shown by FIG. 8, a mouse administered with the polypeptide A-C displays a significant increase in the surface ratio ($\beta$-cells/$\alpha$-cells) $\beta$-cells to $\alpha$-cells. That effect is excellent when polypeptide A is administered.

INDUSTRIAL APPLICABILITY

The present invention may be applied to industry in that it provides an insulin secretion inducer, insulin secretion-inducing composition and a method of manufacturing the same, an accelerator for increasing the number of pancreatic β-cells, a composition for increasing the number of pancreatic β-cells and a method of manufacturing same, in addition to a virus vector for genetic treatment, for use primarily in the treatment of diabetes and of various other diseases.

The invention claimed is:

1. A method of treatment of diabetes or reduction in pancreatic β-cells, said method comprising administering a pharmaceutical composition to a subject in need thereof, the pharmaceutical composition including at least one of the following active ingredients (a) to (f):

(a) a polypeptide having an amino acid sequence encoded by DNA having a base sequence as set forth in SEQ. ID. No. 1 or SEQ. ID. No. 4;

(b) a polypeptide having an insulin secretion inducing action and/or an action of increasing the number of pancreatic β-cells, and having an amino acid sequence in which one amino acid has been substituted, deleted and/or added to an amino acid sequence encoded by DNA having a base sequence as set forth in SEQ. ID. No. 1 or SEQ. ID. No. 4;

(c) a fragment of the polypeptide in (a) or (b) having an insulin secretion inducing action and/or an action of increasing the number of pancreatic β-cells, said fragment comprising the amino acid sequence set forth in SEQ ID NO:10 or SEQ ID NO:11 or SEQ ID NO:12;

(d) a polypeptide having an amino acid sequence as set forth in SEQ. ID. No. 3 or SEQ. ID. No. 6;

(e) a polypeptide having an insulin secretion inducing action and/or an action of increasing the number of pancreatic β-cells, and having an amino acid sequence in which one amino acid has been substituted, deleted and/or added to an amino acid sequence as set forth in SEQ. ID. No. 3 or SEQ. ID. No. 6; and (f) a fragment of the polypeptide in (d) or (e) having an insulin secretion inducing action and/or an action of increasing the number of pancreatic β-cells, said fragment comprising the amino acid sequence set forth in SEQ ID NO:10 or SEQ ID NO:11 or SEQ ID NO:12.

2. The method of claim 1 wherein the active ingredient is a fragment of a polypeptide having an amino acid sequence as set forth in SEQ. ID. NO. 3 or SEQ. ID. No. 6, said fragment consisting of the amino acid sequence set forth in SEQ. ID. NO. 10, SEQ. ID. No. 11 or SEQ. ID. No. 12.

* * * * *